US010166202B2

(12) United States Patent
Berry et al.

(10) Patent No.: US 10,166,202 B2
(45) Date of Patent: Jan. 1, 2019

(54) TREATMENT OF HEPATIC ENCEPHALOPATHY AND LIVER CIRRHOSIS

(75) Inventors: Elliot Berry, Jerusalem (IL); Yosefa Avraham, Jerusalem (IL); Raphael Mechoulam, Jerusalem (IL); Yaron Ilan, Givat Massua (IL); Yossi Dagon, Ness Ziona (IL); Iddo Magen, Kfar Shmuel (IL); Nicholas Grigoriadis, Panorama (GR); Theofilos Poutachidis, Ano Toumpa (GR)

(73) Assignees: Yissum Research Development Company of the Hebrew University of Jerusalem, Jerusalem (IL); Hadasit Medical Research Services & Development Ltd., Jerusalem (IL); Aristotle University of Thessaloniki, Thessaloniki (GR)

( * ) Notice: Subject to any disclaimer, the term of this patent is extended or adjusted under 35 U.S.C. 154(b) by 0 days.

(21) Appl. No.: 13/162,160

(22) Filed: Jun. 16, 2011

(65) Prior Publication Data

US 2011/0251290 A1 Oct. 13, 2011

Related U.S. Application Data

(60) Division of application No. 12/429,832, filed on Apr. 24, 2009, which is a continuation-in-part of application No. PCT/IL2007/001300, filed on Oct. 25, 2007.

(60) Provisional application No. 60/929,444, filed on Jun. 27, 2007, provisional application No. 60/929,443, filed on Jun. 27, 2007, provisional application No. 60/854,073, filed on Oct. 25, 2006.

(51) Int. Cl.
| | |
|---|---|
| A61K 31/05 | (2006.01) |
| A61K 31/09 | (2006.01) |
| A61K 31/165 | (2006.01) |
| A61K 31/232 | (2006.01) |
| A61K 31/352 | (2006.01) |

(52) U.S. Cl.
CPC .............. A61K 31/05 (2013.01); A61K 31/09 (2013.01); A61K 31/165 (2013.01); A61K 31/232 (2013.01); A61K 31/352 (2013.01); Y02A 50/423 (2018.01)

(58) Field of Classification Search
CPC .... A61K 31/05; A61K 32/352; A61K 31/165; A61K 31/09; A61K 31/232; Y02A 50/423
See application file for complete search history.

(56) References Cited

U.S. PATENT DOCUMENTS

| | | | |
|---|---|---|---|
| 6,900,216 B2 * | 5/2005 | Doyle et al. ............... | 514/259.2 |
| 7,320,805 B2 | 1/2008 | Grenard et al. | |
| 7,906,156 B2 | 3/2011 | Grenard et al. | |
| 2005/0143448 A1 * | 6/2005 | Grenard ................ | A61K 45/06 |
| | | | 514/454 |

FOREIGN PATENT DOCUMENTS

WO      WO 0167890 A2 *     9/2001         ............... A23L 1/09

OTHER PUBLICATIONS

"Hepatic encephalopathy: molecular mechanisms underlying the clinical syndrome" by Albrecht et al., J. Neurolog. Sci. 170, 138-46 (1999).*
"Cannabidiol and (–)D9-tetrahydrocannabinol are neuroprotective antioxidants" by Hampson et al., Proc. Nat'l Acad. Sci. USA 95, 8268-73 (1998).*
"Drug Absorption, Bioavailability, and Routes of Administration" in Goodman & Gilman's The Pharmacological Basis of Therapeutics, McGraw-Hill (New York), pp. 5-9 (1996).*
"Effects of Cannabidiol (CBD) on Regional Cerebral Blood Flow" by Crippa et al., Neuropsychopharm. 29, 417-26 (2004).*
"Hepatic Steatosis (Fatty Liver) and Nonalcoholic Steatohepatitis" in Harrison's Principles of Internal Medicine, 15$^{th}$ Ed., McGraw-Hill (New York), pp. 1767-1768 (2001).*
Bornheim, Effect of Cytochrome P450 Inducers on Cocaine-Mediated Hepatotoxicity, 1998, Toxicology and Applied Pharmacology, 150, 158-165.*
Definition of Hepatotoxicity,2009, Mosby's Medical Dictionary, 8th Edition, Elsevier.*
Gonzalez, Role of cytochromes p450 in chemical toxicity and oxidative stress: studies with CYP2E1, 2005, Mutation Research, 569, 101-110.*
Narimatsu et al. (Chem. Pharm. Bull. 1990, 38, 1365).*
Orellana et al. (Hepatology Research, Jan. 2006, 34, 57-63, abstract only).*
Yamada (The Journal of Toxicological Sciences, 1998, 23, 395-402).*
Russo et al. (Neurochemical Research, Aug. 2005, 30, 1037-1043).*
Cardiovascular complications of liver disease, Bomzon and Blendis, eds., CRC Press, Inc., Boca Raton, FL, 1990, pp. 9-10.
El Hiba et al., "Increased Reissner's fiber material in the subcommissural organ and ventricular area in bile duct ligated rats," Acta Histochem 114:676-681 (2012) [Abstract only attached].
Nedungadi et al, "Region specific changes in TRPV channel expression in the vasopressin magnocellular system in hepatic cirrhosis induced hyponatremia," J Neuroendocrinol 24:642-652 (2012).
Pereira et al., "Development of hepatorenal syndrome in bile duct ligated rats," World J Gastroenterol 14:4505-4511 (2008).

(Continued)

*Primary Examiner* — Dennis Heyer
*Assistant Examiner* — Daniel M Podgorski
(74) *Attorney, Agent, or Firm* — Browdy and Neimark, PLLC

(57) ABSTRACT

The compounds D9-tetrahydrocannabinol (THC), cannabidiol (CBD) and capsaicin are useful for prevention, treatment, or both, of hepatic encephalopathy. The compounds capsaicin, 2-arachidonoylglycerol (2-AG), HU-308 and cannabidiol are useful for prevention, treatment, or both, of liver cirrhosis.

4 Claims, 26 Drawing Sheets
(2 of 26 Drawing Sheet(s) Filed in Color)
Specification includes a Sequence Listing.

(56) References Cited

OTHER PUBLICATIONS

Zhang and Fallon, "Hepatopulmonary syndrome: update on pathogenesis and clinical features," Nat Rev Gastroenterol Hepatol 9:539-549 (2012) [Abstract only attached].
Singal et al., "Antioxidants as Therapeutic Agents for Liver Disease" Liver Int., November; 31(10): 1432-1448 (2011).
Dagon, et al., "Cannabinoids ameliorate cerebral dysfunction following liver failure via AMP-activated protein kinase," Faseb journal, 2007, pp. 2431-2441, vol. 21, No. 10.
Avraham, et al., "Endocannabinoids affect neurological and cognitive function in thioacetamide-induced hepatic encephalopathy in mice," Neurobiology of disease, 2006, pp. 237-245, vol. 21, No. 1, Blackwell Science, Oxford, GB.
Julien, et al., "Activation of cannabinoid receptors leads to apoptosis of human hepatic myofibrblasts," Hepatology, 2002, p. 260A, vol. 36, No. 4 part 2, Williams and Wilkins, Baltimore, MD.
Gabbay, et al., "Endocannabinoids and liver disease—review," Liver international, 2005, pp. 921-926, vol. 25, No. 5, Blackwell Munksgaard, Oxford, GB.
Kola, et al., "Cannabinoids and ghrelin have both central and peripheral metabolic and cardiac effects via AMP-activated protein kinase," Journal of biological chemistry, 2005, pp. 25196-25201, vol. 280, No. 26.
Baker, et al., "The therapeutic potential of cannabis," Lancet neurology, 2003, pp. 291-298, vol. 2.
Di Marzo, et al., "Interactions between synthetic vanilloids and the endogenous cannabinoid system," Febs letters, 1998, pp. 449-454, vol. 436.
Mishima, et al., "Characteristics of Learning and Memory Impairment Induced by Δ9-Tetranydrocannabinol in Rats," Jpn J Pharmacol, 2001, pp. 297-308, vol. 87.
Mozsik et al., "Gastroprotection induced by capsaicin in healthy human subjects", World J. Gastroenterol. 11:5180-84 (2005).
Li et al., "Effect of neonatal capsaicin treatment on haemodynamics and renal function in cirrhotic rats", Gut 52:293-99 (2003).
Song et al., "Disordered central cardiovascular regulation in portal hypertensive and cirrhotic rats" Am. J. Physiol. Gastrointest. Liver Physiol. 280:G420-30 (2001).
"Drug Absorption, Bioavailability, and Routes of Administration" in Goodman & Gilman's The Pharmacological Basis of Therapeutics, McGraw-Hili (New York), pp. 5-9 (1996).
Lizardi-Cervera et al., "Hepatic encephalopathy: A review", Ann. Hepatol. 2:122-30 (2003).
Narimatsu et al "Suppression of Liver Microsomal Drug-metabolizing Enzyme Activities in Adult Female Rates Pretreated with Cannabidiol," Biol. Pharm. Bull. 16:428-430 (1993).
Martignoni, et al., "Species differences between mouse, rat, dog, monkey and human cytochrome P450-mediated drug metabolism" in: Species and strain differences in drug metabolism in liver and intestine, Martignoni, M., University Library Groningen[Host], 2006.
Vickers et al., "Serotonin receptor ligands and the treatment of obesity" Curr Opin Investig Drugs, 5(4):377-88 (2004) (Abstract only).
Non-Final Office Action for U.S. Appl. No. 11/934,470, dated Sep. 26, 2009.
Fiers, et al., "More than one way to die: apoptosis, necrosis and reactive oxygen damage" Oncogene, 18:7719-7730 (1999).
"Oxidative stress" Wikipedia, downloaded from https://en.wikipedia.org/wiki/Oxidative_stress, on Feb. 23, 2017.
Berlot et al., The Natural Course of Non-Alcoholic Fatty Liver Disease, Int. J. Mol. Sci. 17(774):1-12 (2016).
Mehta et al., Natural History of Nonalcoholic Fatty Liver Disease, Clinical Liver Disease 1(4):112-113 (2012).
Puri et al., Nonalcoholic Fatty Liver Disease: Definitions, Risk Factors, and Workup, Clinical Liver Disease 1(4):99-103 (2012).
Elpek et al., Cellular and molecular mechanisms in the pathogenesis of liver fibrosis: An update, World Journal of Gastroenterology 20(23): 7260-7276 (2014).
Mukhopadhyay et al., Cannabidiol protects against hepatic ischemia/reperfusion injury by attenuating inflammatory signaling and response, oxidative/nitrative stress, and cell death, Free Radical Biology & Medicine 50:1368-1381 (2011).
Poli et al., Pathogenesis of liver fbrosis: role of oxidative stress, Molecular Aspects of Medicine 21:49-98 (2000).

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Primer specific for CB1

<400> SEQUENCE: 1
ggagaacatc cagtgtgggg                                                      20

<210> SEQ ID NO 2
<211> LENGTH: 20
<212> TYPE: DNA
<213> ORGANISM: Artificial
<220> FEATURE:
<223> OTHER INFORMATION: Primer specific for CB1

<400> SEQUENCE: 2
cattggggct gtctttacgg                                                      20

<210> SEQ ID NO 3
<211> LENGTH: 21
<212> TYPE: DNA
<213> ORGANISM: Artificial
<220> FEATURE:
<223> OTHER INFORMATION: Primer specific for CB2

<400> SEQUENCE: 3
gggtcctctc agcattgatt t                                                    21

<210> SEQ ID NO 4
<211> LENGTH: 23
<212> TYPE: DNA
<213> ORGANISM: Artificial
<220> FEATURE:
<223> OTHER INFORMATION: Primer specific for CB2

<400> SEQUENCE: 4
gttaacaagg cacagcatgg aac                                                  23

<210> SEQ ID NO 5
<211> LENGTH: 20
<212> TYPE: DNA
<213> ORGANISM: Artificial
<220> FEATURE:
<223> OTHER INFORMATION: Primer specific for actin
```

```
<400> SEQUENCE: 5
cagcttcttt gcagctcctt                                              20

<210> SEQ ID NO 6
<211> LENGTH: 19
<212> TYPE: DNA
<213> ORGANISM: Artificial
<220> FEATURE:
<223> OTHER INFORMATION: Primer specific for actin

<400> SEQUENCE: 6
tcacccacat aggagtcct                                               19
```

TREATMENT OF HEPATIC ENCEPHALOPATHY AND LIVER CIRRHOSIS

CROSS-REFERENCE TO RELATED APPLICATIONS

The present application is a divisional of application Ser. No. 12/429,832, filed Apr. 24, 2009, which is a continuation-in-part of international application no. PCT/IL07/001300, filed Oct. 25, 2007, which claims the benefit of three U.S. provisional application Nos. 60/854,073, filed Oct. 25, 2006, 60/929,443, filed Jun. 27, 2007 and 60/929,444, filed Jun. 27, 2007. The entire content of the above applications are incorporated herein by reference.

FIELD OF THE INVENTION

The present invention relates to a composition and methods for the treatment or prevention of hepatic encephalopathy and liver cirrhosis.

BACKGROUND OF THE INVENTION

Cirrhosis is a consequence of acute and chronic liver disease characterized by replacement of liver tissue by fibrotic scar tissue as well as regenerative nodules, leading to progressive loss of liver function. Cirrhosis is most commonly caused by alcoholism, hepatitis C, toxins and fatty liver but has many other possible causes.

Ascites (fluid retention in the abdominal cavity) is the most common complication of cirrhosis and is associated with a poor quality of life, increased risk of infection, and a poor long-term outcome. Other potentially life-threatening complications are hepatic encephalopathy and bleeding from esophageal varices. Today, cirrhosis is generally irreversible once it occurs, and treatment generally focuses on preventing progression and complications. In advanced stages of cirrhosis the only option is a liver transplant.

Modern medicine defines hepatic encephalopathy (HE) as a neuropsychiatric syndrome, which is associated with acute or chronic liver dysfunction and has quantitatively and qualitatively distinct features relating to its severity. In cirrhosis, cerebral dysfunction is heterogeneous ranging from mild neuropsychiatric and psychomotor dysfunction, impaired memory, increased reaction time, sensory abnormalities and poor concentration to severe features such as confusion, stupor, coma and eventually death.

Hepatic encephalopathy is caused by disorders affecting the liver including disorders that reduce liver function (such as cirrhosis or hepatitis) and conditions where there is impaired blood circulation in the liver.

While the symptoms of hepatic encephalopathy are well documented, its pathogenesis is not clear yet and a number of possible scenarios have been suggested. First, liver failure induces impaired glucose oxidative pathways and increased lactate synthesis in the brain which results in energy failure. Second, hypoglycemia and hypoxia are also major contributors to the energy failure seen in hepatic encephalopathy. Third, ammonia is considered to play a major role in the pathogenesis of the neuropsychiatric disturbances observed in hepatic encephalopathy. The liver is the major organ for detoxifying ammonia. When the liver fails the body is incapable of efficiently converting ammonia to urea or glutamine, resulting in systemic hyperammonemia including the brain. Unlike the liver, the brain lacks an effective urea cycle and therefore relies entirely on glutamine synthesis for the removal of blood-borne ammonia. Since glutamine synthetase is dependent on an adequate level of ATP to amidate glutamate to glutamine, ammonia intoxication results in depletion of brain ATP resources and eventually cell death (Ott et al., 2005; Hardie, 2004). Finally, decreased glucose utilization in the brain may be compensated by mobilization of amino acids to provide carbon skeletons as substrates for energy metabolism. Yet, attempts to balance energy failure at the expense of cerebral proteins may end in destructive brain proteolysis (Hardie and Carling, 1997).

However, other factors such as an inflammatory response and astrogliosis in the brain are also implicated in hepatic encephalopathy.

The AMP-activated protein kinase (AMPK) is an evolutionarily conserved metabolic master switch. AMPK is allosterically activated by 5'-AMP, which accumulates following ATP hydrolysis. Conversely, high ATP antagonizes the activating effects of 5'-AMP on AMPK. AMP binding to AMPK leads to activation of the enzyme by inducing a conformational change exposing threonine-172 in the catalytic domain, which undergoes phosphorylation by an upstream AMPK kinase (AMPKK) (Hawley et al., 1996). Once activated, it switches on catabolic pathways (such as fatty acid oxidation and glycolysis) and switches off ATP-consuming pathways (such as lipogenesis) both by short-term effect on phosphorylation of regulatory proteins and by long-term effect on gene expression (Foretz et al., 2006). Stresses such as nutrient depletion, hypoxia, heat shock, metabolic poisoning and exercise, all activate AMPK by their effect on the ratio of 5'-AMP to ATP. AMPK, in turn, phosphorylates multiple targets, which switch off anabolic pathways and stimulate catabolic ones. AMPK was recently recognized as a key regulator of whole body energy metabolism (Minokoshi et al., 2004). Cerebral AMPK responds to integration of nutritional and hormonal input. Hypothalamic AMPK controls energy balance via regulation of food intake, body weight and glucose and lipid homeostasis (Dagon et al., 2005; Pagotto et al., 2005). Hippocampal AMPK controls cognitive function via regulation of neurogenesis and neuroapoptosis (Dagon et al, 2005).

The cannabinoid (CB) system consists of two receptor subtypes. The CB-1 receptors are predominantly found in the brain, while the CB-2 receptors are mostly found in the peripheral tissue (Matsuda, et al., 1990). The main endogenous endocannabinoids are small molecules derived from membrane arachidonic acid, such as anandamide(arachidonoylethanolamide) and 2-arachidonoylglycerol (2-AG) (Iversen, 2000; Berry et al., 2002). D9-tetrahydrocannabinol (THC), the major psychoactive constituent of the Cannabis plant, is a cannabinoid agonist which produces a myriad of complex pharmacological effects (Baker et al., 2003; Avraham et al., 2006). It is now recognized that most of the central effects of endogenous as well as exogenous cannabinoids are mediated through the CB-1 receptor, a family of G-protein-coupled receptors. Cerebral CB-1 receptors are part of the complex mechanisms involved in the control of energy balance via regulation of food intake and body weight (Teixeira-Clerc et al., 2006). The endocannabinoid system has also been demonstrated to exert neuroprotective effects in several types of cerebral insults via regulation of motor control, cognition, emotional responses, motivated behavior and homeostasis (Julien et al., 2005).

The endocannabinoid system was shown to have an important role in the pathogenesis of hepatic encephalopathy. Modulation of this system, either by specific antagonists to the CB1 cannabinoid receptor, or by agonists specific for the CB2 receptor, such as HU-308 was shown to be effective (Avraham et al., 2006).

SUMMARY OF THE INVENTION

The present invention is based on the surprising finding that D9-tetrahydrocannabinol (THC) is effective in the treatment of hepatic encephalopathy. This finding is surprising in view of the fact that THC was previously known to have about equal affinity both to the CB1 and the CB2 receptors and the above-mentioned Avraham et al, 2006 publication teaches that modulation of the endocannabinoid system is effected either by specific antagonists to the CB1 cannabinoid receptor or by agonists specific for the CB2 receptor.

The present invention is further based on the findings that cannabidiol (CBD) and capsaicin are effective in the treatment of hepatic encephalopathy. This finding is also surprising since cannabidiol does not exert its physiological activity through neither of the CB1 or the CB2 receptors while capsaicin is known to act through the vanilloid receptors subtype 1.

Accordingly, the present invention relates to a compound selected from D9-tetrahydrocannabinol (THC), cannabidiol or capsaicin, comprising said compound, for prevention, treatment, or both, of hepatic encephalopathy.

The present invention also relates to pharmaceutical composition comprising a compound selected from D9-tetrahydrocannabinol (THC), cannabidiol or capsaicin, for prevention, treatment, or both, of hepatic encephalopathy.

Furthermore a method for prevention, treatment, or both, of hepatic encephalopathy comprising administering to a subject in need an effective amount of a compound selected from the group consisting of D9-tetrahydrocannabinol, cannabidiol and capsaicin, is provided.

The term "hepatic encephalopathy", in the context of the invention, and in accordance with the World Congress of Gastroenterology 1998 in Vienna, refers to all subclasses of the disease as follows: Type A (acute), hepatic encephalopathy associated with acute liver failure; type B (bypass), caused by portal-systemic shunting without associated intrinsic liver disease; and type C (cirrhosis), occurring in patients with cirrhosis.

This term refers to all durations and characteristics of hepatic encephalopathy and includes episodic, persistent and minimal. The term "minimal encephalopathy" refers to patients with cirrhosis who do not demonstrate clinically overt cognitive dysfunction, but who show a cognitive impairment on neuropsychological studies.

The evaluation of severity of persistent hepatic encephalopathy is based on the West Haven Criteria for semi-quantitative grading of mental status, referring to the level of impairment of autonomy, changes in consciousness, intellectual function, behavior, and the dependence on therapy, and includes: Grade 1—trivial lack of awareness; euphoria or anxiety; shortened attention span; impaired performance of addition. Grade 2—lethargy or apathy; minimal disorientation for time or place; subtle personality change; inappropriate behavior; impaired performance of subtraction. Grade 3—somnolence to semistupor, but responsive to verbal stimuli; confusion; gross disorientation. Grade 4—Coma (unresponsive to verbal or noxious stimuli).

The term "treatment" in the context of the present invention refers to at least one of the following: decrease in the severity of at least one undesired side effect associated with the disease; improvement in the overall cognitive function of the treated subject; delay in the progression from one disease stage to the other; shortening the length of an hepatic encephalopathy episode and lengthening the period between episodes.

The term "treatment" is also meant to refer to preventive or prophylactic treatment—meaning that a person known to have liver dysfunction or to be at risk for developing liver dysfunction (for example, due to hepatitis C) is administered with THC, cannabidiol or capsaicin, even before manifestation of hepatic encephalopathy in order to prevent its occurrence.

The terms "THC" or "D9-tetrahydrocannabinol" are used herein interchangeably for the compound (−)-(6aR,10aR)-6,6,9-trimethyl-3-pentyl-6a,7,8,10a-tetrahydro-6H-benzo[c]chromen-1-ol. This substance may be isolated from the natural source (cannabis), for example, in accordance with the method in Gaoni and Mechoulam (1964) or may be synthetically produced such as dronabinol, which is available as a prescription drug (under the trade name Marinol™ of Unimed Pharmaceuticals, Inc.)

The present invention also relates to a compound selected from capsaicin, 2-arachidonoylglycerol (2-AG), HU-308 or cannabidiol for prevention, treatment, or both, of liver cirrhosis.

The invention further relates to the use of capsaicin, cannabidiol (CBD), 2-arachidonoylglycerol or HU-308 for the preparation of a medicament for prevention, treatment, or both, of liver cirrhosis.

Furthermore the invention concerns a method for the prevention, treatment, or both, of liver cirrhosis comprising administering to a subject a therapeutically effective amount of capsaicin, cannabidiol, 2-arachidonoylglycerol or HU-308.

The term "liver cirrhosis" as used herein refers to any stage in the development of the pathological condition, from very initial development of fibrotic scar tissue to full-blown liver cirrhosis. Examples of diseases or conditions that are known to lead to liver cirrhosis are, but are not limited to: alcoholic liver disease, chronic viral hepatitis (Type B and C), chronic bile duct blockage, metabolic diseases resulting in abnormal storage of copper (Wilson's disease) or iron (Hemochromatosis). Cirrhosis may also be caused by exposure to drugs and toxins, by autoimmune processes such as autoimmune hepatitis, by inherited diseases such as cystic fibrosis and alpha antitrypsin deficiency, and by obesity (so called "fatty liver" or nonalcoholic steatohepatitis). Furthermore, severe reactions to prescription drugs, prolonged exposure to environmental toxins such as arsenic, the parasitic infection schistosomiasis, and repeated bouts of heart failure with liver congestion can all lead to cirrhosis.

The treatment may be initiated when a disease is established to stop or slow disease progression. Alternatively, as many of the conditions (e.g. hepatitis, excessive consumption of alcohol and obesity) are evident long before cirrhosis develops, often many years before, capsaicin, cannabidiol, 2-AG or HU-308 may be given in a preventive prophylactic manner to prevent or delay the onset of cirrhosis.

BRIEF DESCRIPTION OF THE FIGURES

The patent or application file contains at least one drawing executed in color. Copies of this patent or patent application publication with color drawings will be provided by the Office upon request and payment of the necessary fee.

In some of the following figures, the level of significance of differences between treatment groups is designated with one, two or three asterisks(s).

FIG. 4C, Centrilobular coagulative necrosis (score=2); 4D, Central to central (bridging) necrosis (score=3); 4E, massive necrosis effacing liver architecture (score=4); 4F, higher magnification of liver centrilobular area (score=1).

DETAILED DESCRIPTION OF THE INVENTION

Figure 1:
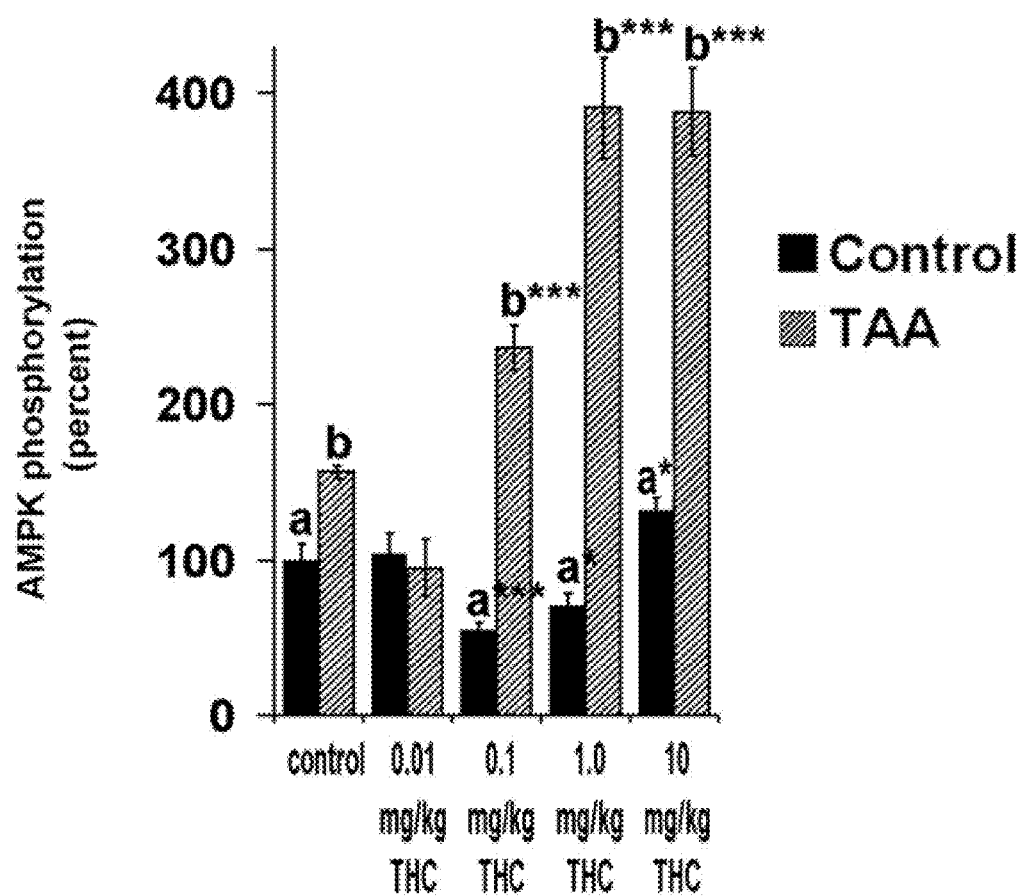
FIG. 1 shows D9-tetrahydrocannabinol (THC)-induced AMPK activation following thioacetamide (TAA)-induced liver failure in mice. Mice were administrated with saline or TAA. After 5 days, mice were treated with 0.1-10 mg/kg THC for 1 h. AMPK expression and phosphorylation on Thr172 were analyzed by immunoblotting. Black columns represent control group and the gray columns represents the TAA-treated group.

Our study shows that AMPK is potently activated in murine models of hepatic encephalopathy. This correlates with the observed hyperammonia and hypoglycemia—two major causes of cerebral energy depletion. Nonetheless, as found in acute hepatotoxicity (caused by TAA), this response decreases with time, and eventually reaches the same level as that of the chronic stress induced by bile duct ligation. Such a cerebral adaptation response fails to meet the intact brain energy requirements and may be augmented by pharmacological means (AICAR).

In light of this, pharmacological activation of AMPK might provide a new strategy for the management of hepatic encephalopathy. However, unselective drugs such as AICAR, which activate AMPK under normal as well as under stress conditions, are not suitable for clinical use. THC, the main active constituent of marijuana, has been repeatedly demonstrated to cause brain dysfunction and neurotoxicity (Mishima et al., 2001). This finding is in line with our observations disclosed herein below of its ability to stimulate AMPK. In addition, these studies have used high dosage of THC (1-15 mg/kg), quantities that we found necessary for AMPK activation under normal circumstances.

It is a finding of the present invention that the quantity of THC required to activate AMPK drops (from 10 mg/kg in healthy animals to 0.1 mg/kg in experimental hepatic encephalopathy animals) as shown herein below. Therefore, THC could be suitable as a selective agent that could function as a "stress specific drug" by activating AMPK only under pathological conditions.

The surprising fact that THC, which has about equal affinity for the CB1 and CB2 receptor, was effective in the treatment of induced hepatic encephalopathy in animal models, motivated us to investigate other compounds known to interact with receptors other than the endocannabinoid receptors. For example, capsaicin, suggested by Di Marzo et al (1998) to interact with the endocannabinoid system, acts on neural cells via vanilloid receptors subtype 1 (VR1, also known as transient receptor potential 1 TRPV1), a non-selective cation channel, which can be blocked by capsazepine. As shown herein below, capsaicin treatment of induced hepatic encephalopathy in animal models resulted in both improved hepatic and brain functions.

A second compound tested herein to treat the animals is cannabidiol, an active ingredient of Cannabis Sativa devoid of adverse effects related to the CB1 receptor owing to its CB1-independent mechanism of action. Cannabidiol is also a very potent anti-inflammatory agent. It is a finding of the present invention that cannabidiol improves impaired brain and liver function in experimental hepatic encephalopathy in animal models. Furthermore, two additional cannabinoids, 2-AG and HU-308 were shown herein to positively affect liver function in experimental hepatic encephalopathy in animal models.

The present invention thus provides a compound selected from D9-tetrahydrocannabinol (THC), cannabidiol and capsaicin for prevention, treatment, or both of hepatic encephalopathy.

In one preferred embodiment the compound is D9-tetrahydrocannabinol. In another preferred embodiment the compound is cannabidiol. In still another preferred embodiment the compound is capsaicin.

The compound may be formulated in any suitable form for administration, preferably in an oral, parenteral, sublingual or intranasal dosage form.

According to the present invention, D9-tetrahydrocannabinol, cannabidiol and capsaicin are intended for prevention and/or treatment of all subclasses of hepatic encephalopathy as described above, i.e. Type A, Type B or Type C, preferably type A or type C.

The present invention further provides a pharmaceutical composition for prevention, treatment, or both, of hepatic encephalopathy comprising a compound selected from D9-tetrahydrocannabinol, cannabidiol and capsaicin and a pharmaceutically acceptable carrier.

The present invention also concerns a method for prevention, treatment, or both, of hepatic encephalopathy comprising administering to a subject in need a therapeutically effective amount of a compound selected from D9-tetrahydrocannabinol (THC), cannabidiol and capsaicin.

In one aspect the present invention relates to a compound selected from capsaicin, 2-arachidonoylglycerol (2-AG), HU-308 or cannabidiol for prevention, treatment, or both, of liver cirrhosis.

The invention further relates to a pharmaceutical composition comprising a compound, selected from capsaicin, 2-arachidonoylglycerol (2-AG), HU-308 or cannabidiol for prevention, treatment, or both, of liver cirrhosis In one preferred embodiment the compound is 2-arachidonoylglycerol. In another preferred embodiment the compound is HU-308. In still another preferred embodiment the compound is capsaicin. In yet another preferred embodiment the compound is cannabidiol.

The term "prevention of liver cirrhosis" refers herein to preventing or slowing the deterioration of any damage caused to the liver tissue, such as the accumulation of fibrotic scar tissue, by factors known to cause cirrhosis such as, but not limited to, alcoholic liver disease, chronic viral hepatitis type C, chronic viral hepatitis type B, chronic bile duct blockage, Wilson's disease, hemochromatosis, exposures to drug and toxins, autoimmune hepatitis, cystic fibrosis, alpha antitrypsin deficiency, obesity or schistosomiasis.

It is envisioned that prevention of the development of liver cirrhosis can be achieved by treating subjects in need, such as alcoholics, people infected with hepatitis C and obese people, at very early stages of their disease or condition, even before appearance of physical symptoms of liver cirrhosis.

The present invention also concerns a method for prevention, treatment, or both, of liver cirrhosis, comprising administering to a subject in need a therapeutically effective amount of a compound selected from capsaicin, 2-arachidonoylglycerol (2-AG), HU-308 or cannabidiol.

The present invention further provides a compound selected from cannabidiol (CBD) or capsaicin for prevention, treatment, or both, of hepatic encephalopathy or liver cirrhosis.

The invention further provides a pharmaceutical composition for prevention, treatment, or both, of hepatic encephalopathy or liver cirrhosis, comprising cannabidiol or capsaicin and a pharmaceutically acceptable carrier.

The invention will now be illustrated by the following non-limiting examples.

EXAMPLES

Materials and Methods (i) Reagents. THC, SR141716A, SR144528 and CBD were provided by Prof. Raphael Mechoulam (Faculty of Medicine and Department of Pharmacology, Hebrew University of Jerusalem). Hepatotoxin thioacetamide (TAA) and capsaicin were obtained from Sigma-Aldrich (Rehovot, Israel). 5-aminoimidazole-4-carboxamide ribonucleoside (AICAR) was obtained from Toronto Research Chemicals (TRC). HU-308 was synthesized as described in Hanus et al. (1999).

(ii) Mice. Eight- to 10-week old female Sabra mice (29-32 g), obtained from the animal facility of the Hebrew University, Israel, were assigned at random to different groups of 10 mice per cage and were used in all experiments. All cages contained wood-chip bedding and were placed in a temperature-controlled room at 22° C., on a 12 h light/dark cycle (lights on at 07.00 a.m.). The mice had free access to water 24 h a day. The food provided was Purina chow, the animals were maintained in the animal facility (SPF unit) of the Hebrew University Hadassah Medical School, Jerusalem. CB-2 KO mice were provided by Prof. Zimmer, Institute of Molecular Psychiatry, University of Bonn, Germany.

Mice were sacrificed after treatment by decapitation between 10.00-12.00 a.m. Brains were rapidly removed and were dissected out and kept at −70° C.

(iii) Induction of hepatic failure (iiia) Bile duct ligation. A midline incision was made under general anesthesia. The common bile duct was localized, doubly ligated, and cut between these two ligatures. In sham animals, a midline incision was performed, but with BDL.

(iiib) TAA. A single dose of 200 mg kg-1 of TAA was injected by the intraperitoneal route (i.p.). 24 hours after injection all animals (including control) were injected (s. c) with 0.5 ml solution of 0.45% NaCl, 5% dextrose and 0.2% KCl in order to prevent hypovolemia, hypokalemia and hypoglycemia. The mice were intermittently exposed to infrared light in order to prevent hypothermia. THC was administered i.p. either alone or with SR141716A on day 6 after TAA administration. Mice were sacrificed 1 h post treatment and analyzed for AMPK level. For the behavioral tests which started on day 6 after TAA administration, THC was administered i.p. during days 6-10. Neurological score, activity and cognitive function were analyzed during these days.

(iv) Immunoblot analysis. Total hippocampal protein was extracted using TriFast reagent (peqLab, Germany). Aliquots of the clarified lysates containing 30 mg protein were denatured in Laemmli sample buffer (6% SDS 30%, glycerol, 0.02% bromophenol blue, 200 mM Tris-HCl (pH 6.8), and 250 mM-mercaptoethanol, at 95° C. for 5 min. The samples were resolved by SDS-PAGE (10% acrylamide), and blotted onto nitrocellulose membrane. Non-specific binding in a Western blot analysis was prevented by immersing the membranes in blocking buffer (5% nonfat dry milk in Tris-buffer saline-Tween 20 (TBS-T)), for 2 h at room temperature. The membranes were then exposed to the indicated antibodies diluted 1:1000 for 1 h at room temperature. Anti-AMPK and phospho-AMPK antibodies were obtained from Cell Signaling. Anti-protein kinase B (AKT) was obtained from Upstate. Anti-actin was from Santa Cruz Biotechnology Inc. (Santa Cruz, Calif.). The blots were rinsed in TBS-T and then incubated with horseradish peroxidase-conjugated goat anti-mouse antibodies (1:10,000; Santa Cruz Biotechnology Inc., Santa Cruz, Calif.) for 1 h at room temperature. Antibody-antigen complexes were visualized by detecting enhanced chemiluminescence with X-ray film.

(v) RT-PCR analysis. Total hippocampal RNA was extracted using TriFast reagent according to the manufacturer's instructions and reverse transcribed. Primers specific for CB1 were GGAGAACATCCAGTGTGGGG [SEQ ID NO: 1] and CATTGGGGCTGTCTTTACGG [SEQ ID NO: 2], for CB2 GGGTCCTCTCAGCATTGATTT [SEQ ID NO: 3], and GTTAACAAGGCACAGCATGGAAC [SEQ ID NO: 4], and for actin CAG CTTCTTTGCAGCTCCTT [SEQ ID NO: 5] and TCACCCACATAGGAGTCCT [SEQ ID NO: 6]. All primers were synthesized by Danyel Biotech, Israel.

(vi) Catecholamine measurements. Catecholamines were measured as described previously (Avraham et al, 1996). The assay for dopamine was performed by High Pressure Liquid Chromatography (HPLC) separation and detection using HPLC-electrochemical detection (ECD). Values are presented as concentration (ng/g tissue).

(vii) Neurological function. Neurological function was assessed by a 10 point scale based on reflexes and task performance (Chen et al., 1996): exit from a circle 1 meter in diameter in less than 1 minute, seeking, walking a straight line, startle reflex, grasping reflex, righting reflex, placing reflex, corneal reflex, maintaining balance on a beam 3, 2 and 1 cm in width, climbing onto a square and a round pole. For each task failed or abnormal reflex reaction a score of 1 was assigned. Thus, a higher score indicates poorer neurological function. The neurological score was assessed one day after TAA induction (day 2). The mice were then divided between treatment groups so that each group had a similar baseline neurological score after TAA induction. The post-treatment neurological score was assessed one day after administration of the agonist or the antagonist or the vehicle (day 3).

(viii) Activity. The activity test was performed on day 4, since in the first 3 days after TAA injection almost no motor activity was observed. One of two methods was utilized: a) an activity apparatus, which consists of a cylindrical chamber (60 cm in diameter) with crossing infrared beams. Locomotor activity was recorded by a counter (attached to the apparatus), that counts the number of beam crossings made by the mice at one-minute intervals. Activity of two mice was measured simultaneously for a five-minute period. Two mice were tested together to lower stress to the minimum. Activity is presented as the mean number of beam crossings in 5 minutes.

Activity was also assessed in the open field (20×30 cm field divided into 12 squares of equal size) as described previously (Fride and Mechoulam, 1993). Two mice were observed simultaneously for 5 minutes. Locomotor activity was recorded by counting the number of crossings by the mice at one minute intervals. Results are presented as the mean number of crossings per minute.

(ix) Eight-arm maze. The animals were placed in an eight-arm maze, which is a scaled-down version of that developed for rats (Olton and Samuelson, 1976; Pick and Yanai, 1983). We used water deprivation achieved by limiting water consumption overnight and a reward of 50 µl of water presented at the end of each arm. The mice were tested until they made entries into all eight arms or until they completed 24 entries, whichever came first. Hence, the lower the score, the better the performance. Maze performance was calculated each day for five consecutive days. Results were presented as area under the curve (AUC) utilizing the formula: (day 2+day 3+day 4+day 5)−4*(day 1).

(x) Statistical analysis. Data are presented as means and standard deviations (SD) or standard errors (SEM). Results were evaluated by one-way ANOVA and 2-tailed t-test. Post-hoc testing was carried out using the Tukey-Kramer multiple comparisons procedure.

(xi) Liver function analysis. Ammonia, bilirubin, ALT, AST, GGT and glucose were analyzed using standard analytical methods in the Hadassah Hospital Biochemistry Department, Jerusalem, Israel.

Example 1

Experimental Hepatic Encephalopathy is Accompanied by Activation of AMPK by Cannabinoids To consider their role in AMPK stimulation, we studied the effects of giving exogenous cannabinoids to activate AMPK. In the first step, control mice were administrated with 0.01 to 10 mg/kg THC and hippocampal AMPK phosphorylation was analyzed. THC treatment showed a biphasic effect (Sulcova et al., 1998). While low levels of THC (less than 0.1 mg/kg) reduced the level of activated AMPK, higher concentrations exhibited a dose dependent elevation in activated enzyme, reaching a significant activation of AMPK (FIG. 1). In the next step, the effect of THC was tested in TAA treated mice. In this instance THC also demonstrated a biphasic effect. However, an inactivating effect was already observed in 0.01 mg/kg and AMPK activation was achieved by 0.1 mg/kg. Elevation of the cerebral responsiveness to THC suggested that low doses of THC, which do not activate the AMPK in the healthy animals, could be used in the pathological state.

Example 2

Figure 2A:
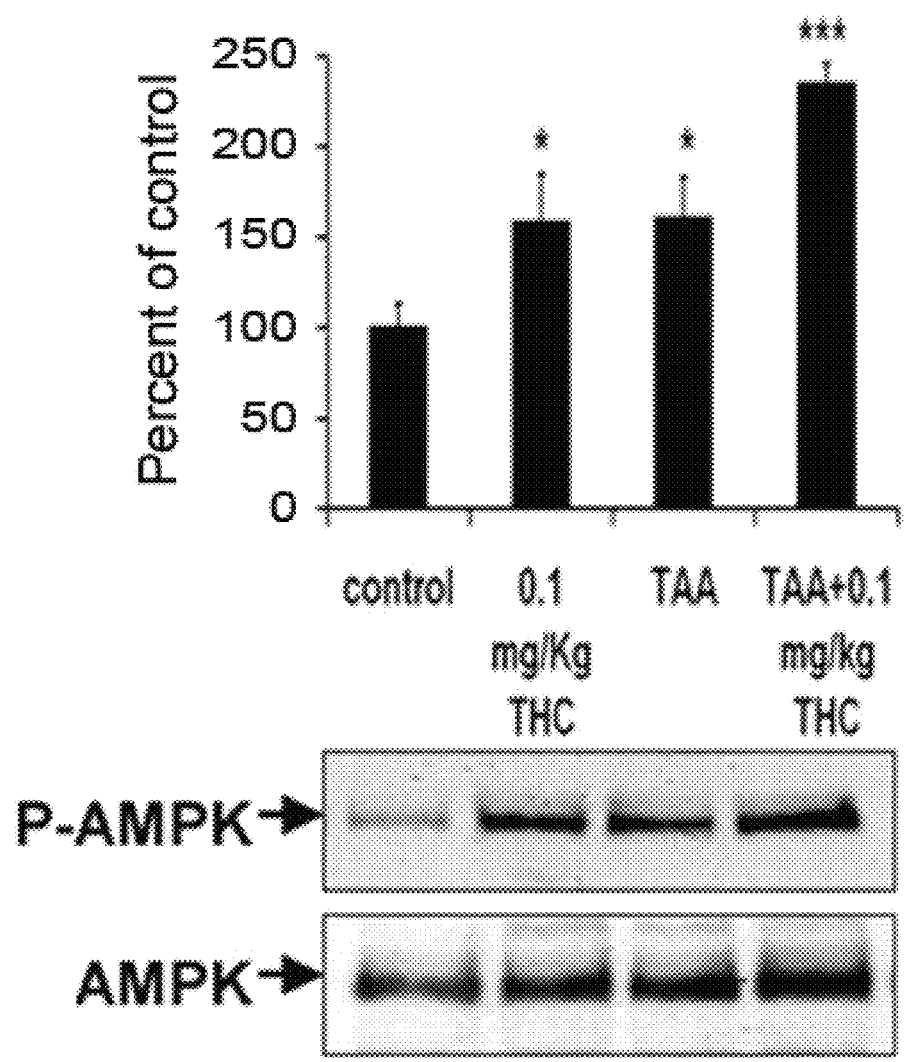
FIGS. 2A-E show that THC activates AMPK and improves impaired brain function in TAA-induced liver failure in mice. Mice were treated with TAA for 5 days, then 0.1 mM THC was administrated daily for 5 days. (2A) Hippocampal AMPK expression and phosphorylation on Thr 172 were analyzed by immunoblotting. P-AMPK, phosphorylated AMPK. (2B) Mice were treated as above and performance in an eight arm maze was measured every day after the THC treatment. AUC, area under the curve. (2C) Activity score. (2D) Neurological score under the same conditions. (2E) Catecholamines levels were analyzed by HPLC. DA, dopamine.

THC Activates AMPK and Improves Impaired Brain Function in Experimental Hepatic Encephalopathy Since treatment of 0.1 mg/kg THC augmented AMPK activation in a similar manner to AICAR treatment, we chose this dose to test THC's physiological effects on the experimental hepatic encephalopathy. TAA treated mice were administrated daily with 0.1 mg/kg THC for 5 days. Amplification of AMPK activation in response to THC administration was confirmed in the brains of the experimental animals at the end of the behavioral studies (FIG. 2A).

Figure 2B:
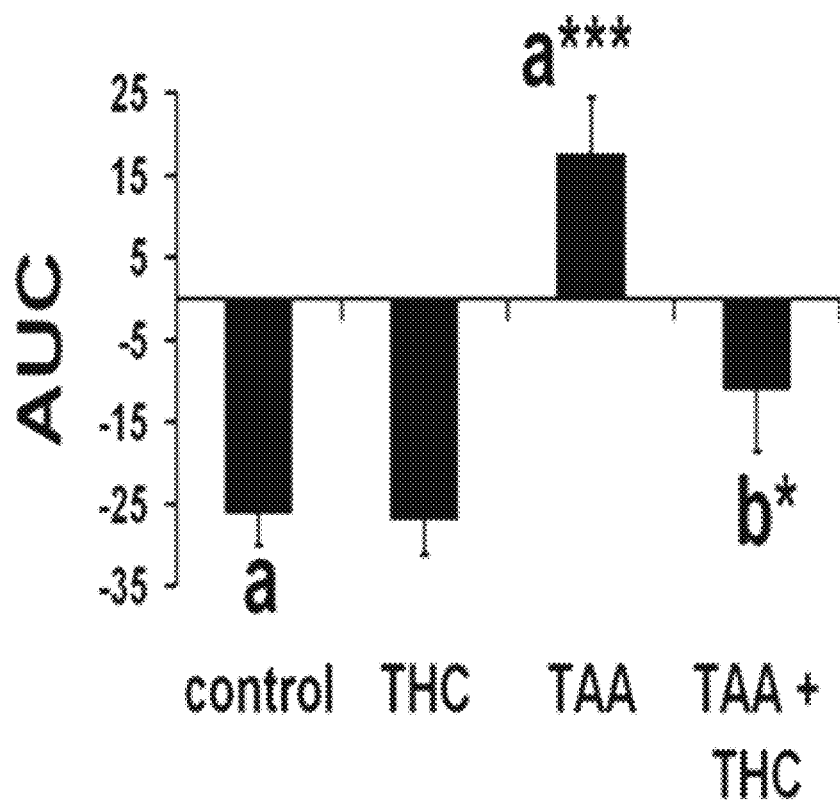
Figure 2C:
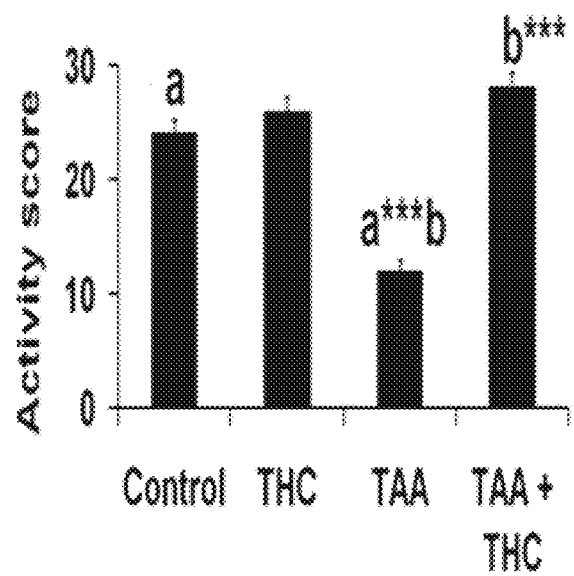
Figure 2D:
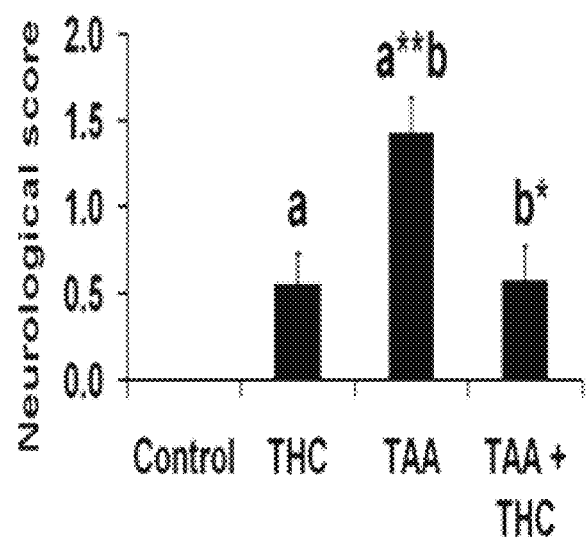
Figure 2E:
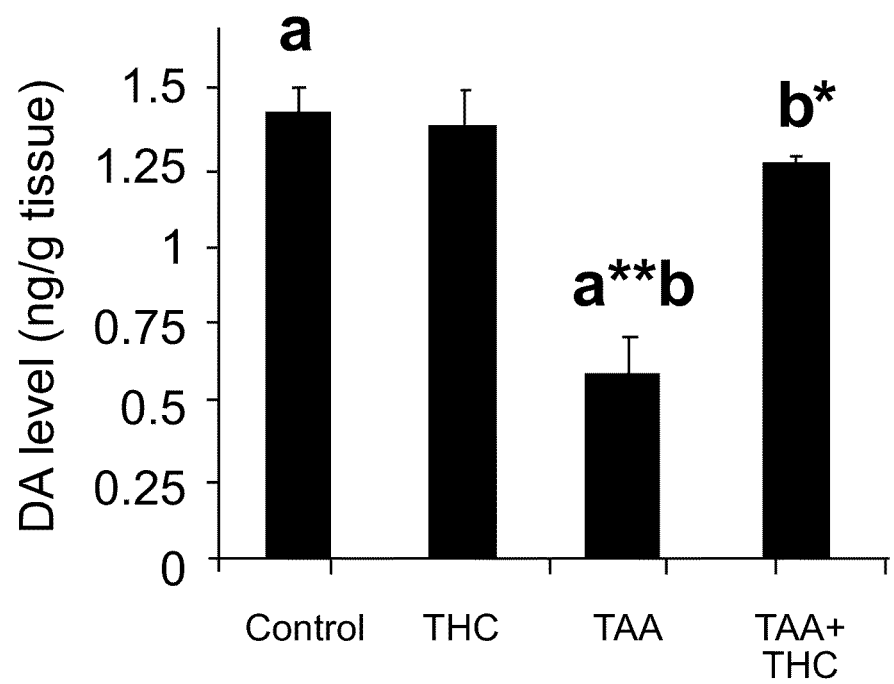

Next, we investigated the outcome of AMPK activation increase on brain function. Following the treatment, TAA-induced impaired cognitive function was improved significantly (FIG. 2B), poor activity performances were restored (FIG. 2C) and the reduced neurological score was improved (FIG. 2D). To reveal the mechanism by which THC could improve brain function, we studied the catecholaminergic response to THC treatment. Brain tissue in animals with experimental hepatic encephalopathy exhibited reduced dopamine concentrations while THC administration, similarly to AICAR administration, restored levels to normal (FIG. 2E). These results demonstrated the potential of THC to stimulate cerebral AMPK activity in treating hepatic encephalopathy.

Example 3

AICAR and THC Treatment do not Improve Markers of Hepatic Function

Figure 3A:
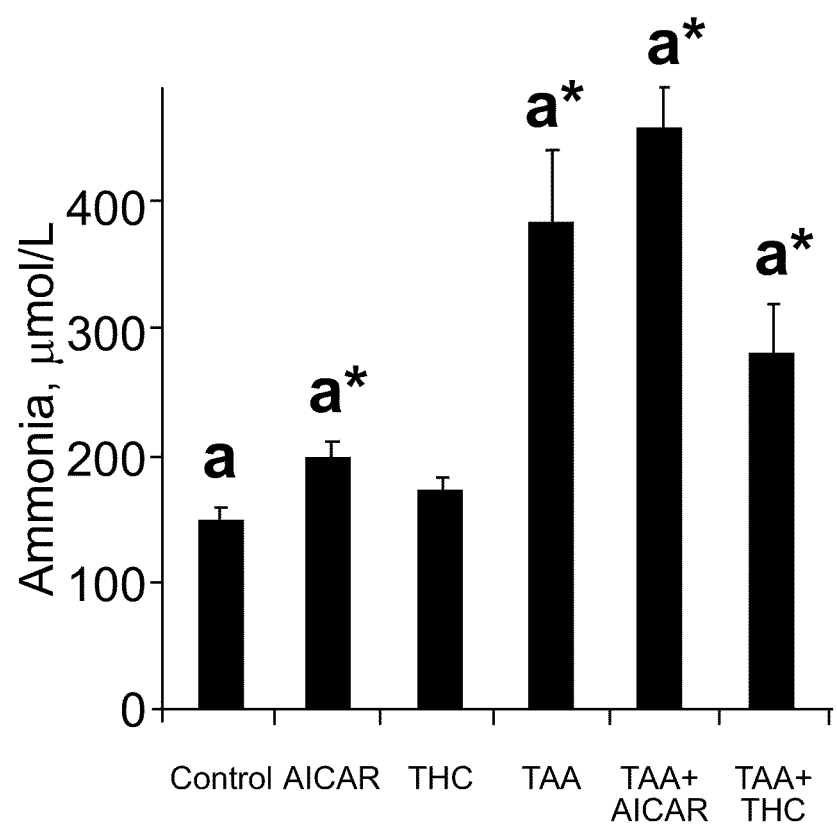
FIGS. 3A-F show the effect of AICAR and THC treatment on hepatic failure. Mice were treated with TAA or saline and then with 0.5 mM AICAR or 0.1 mg/l THC. Blood plasma was obtained for liver functions analysis. (3A) Ammonia; (3B) Bilirubin; (3C) alanine transaminase (ALT); (3D) aspartate aminotransferase (AST); (3E) gamma-glutamyl-transferase (GGT); (3F) Glucose.
Figure 3B:
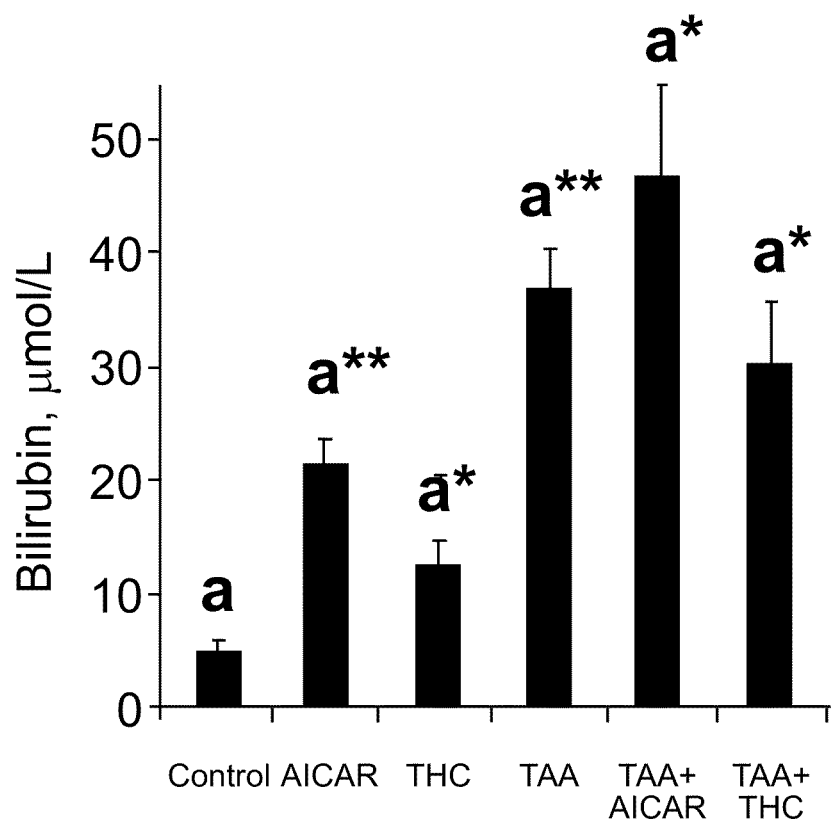
Figure 3C:
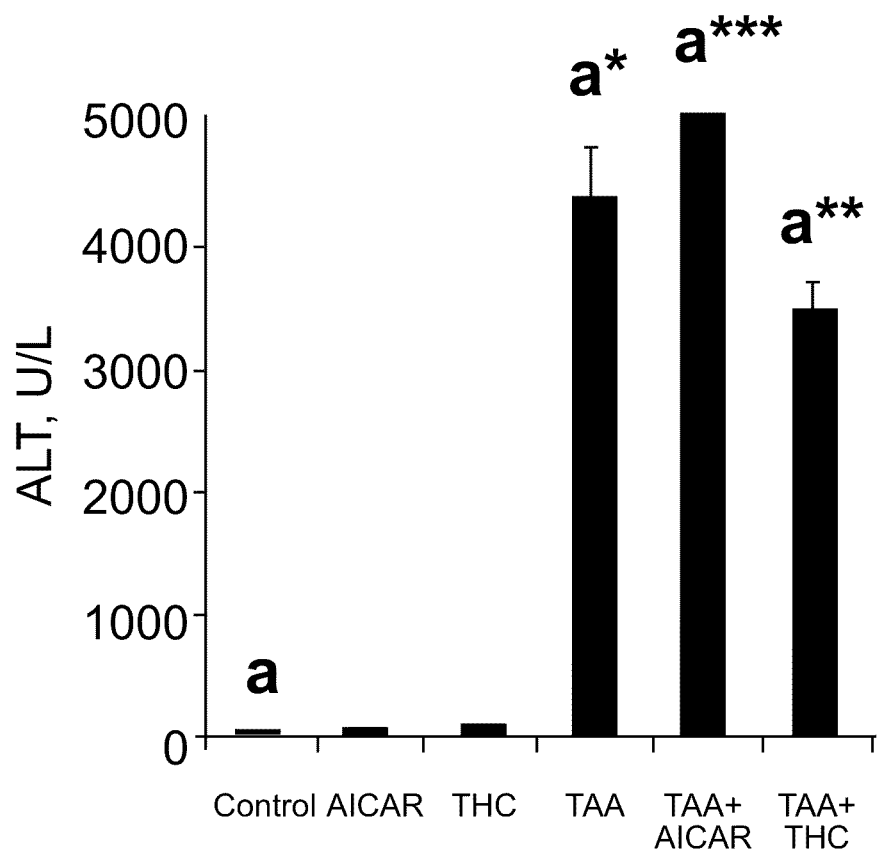
Figure 3D:
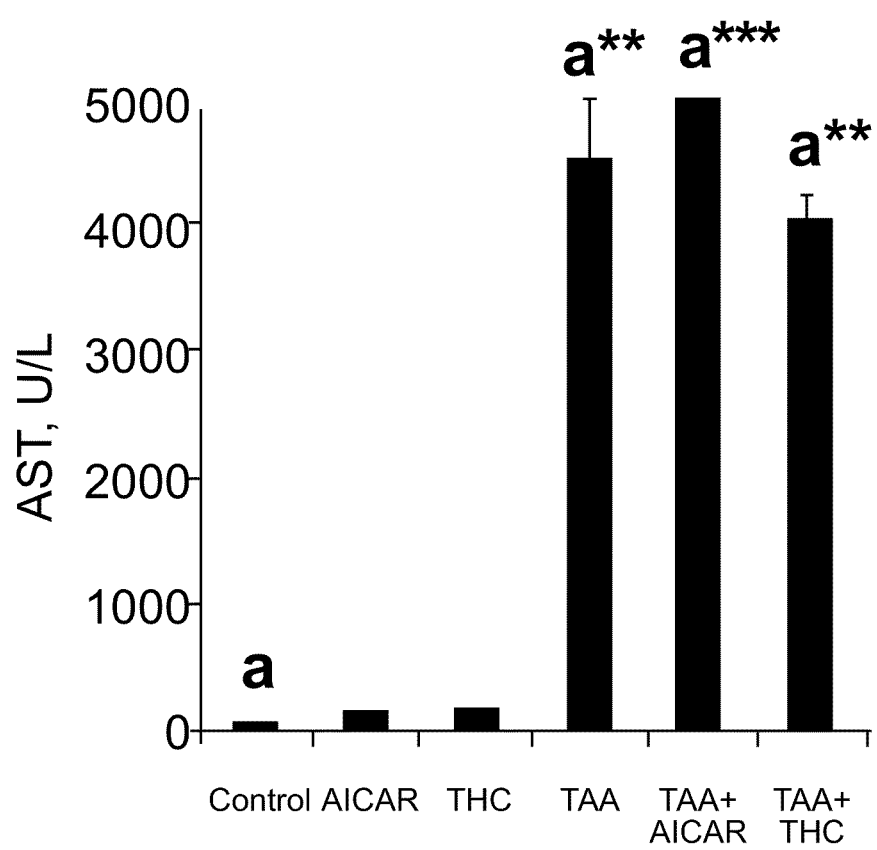
Figure 3E:
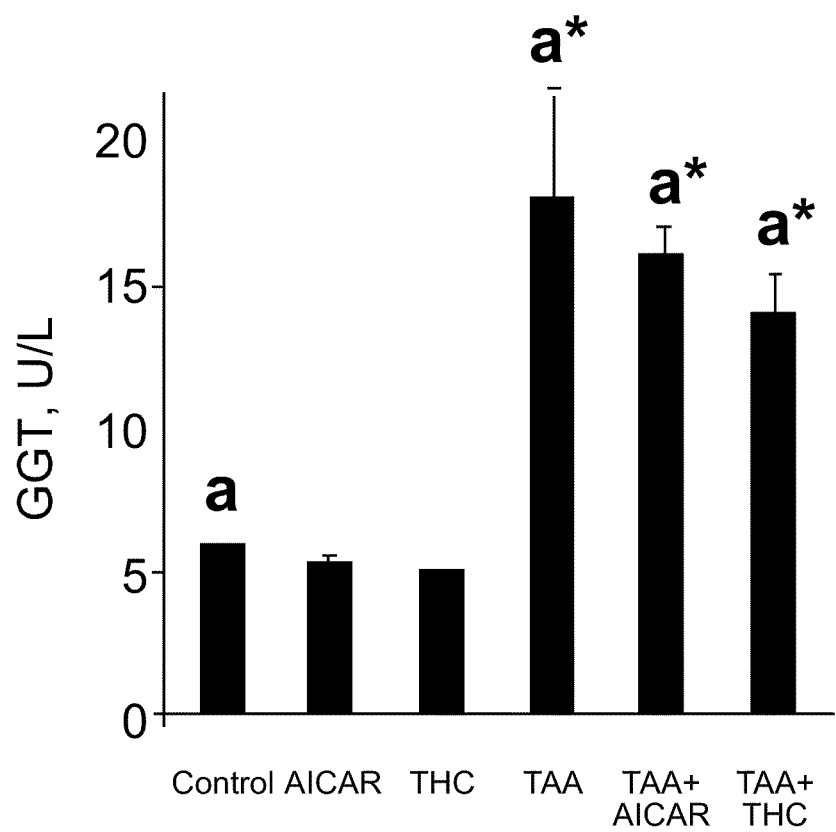
Figure 3F:
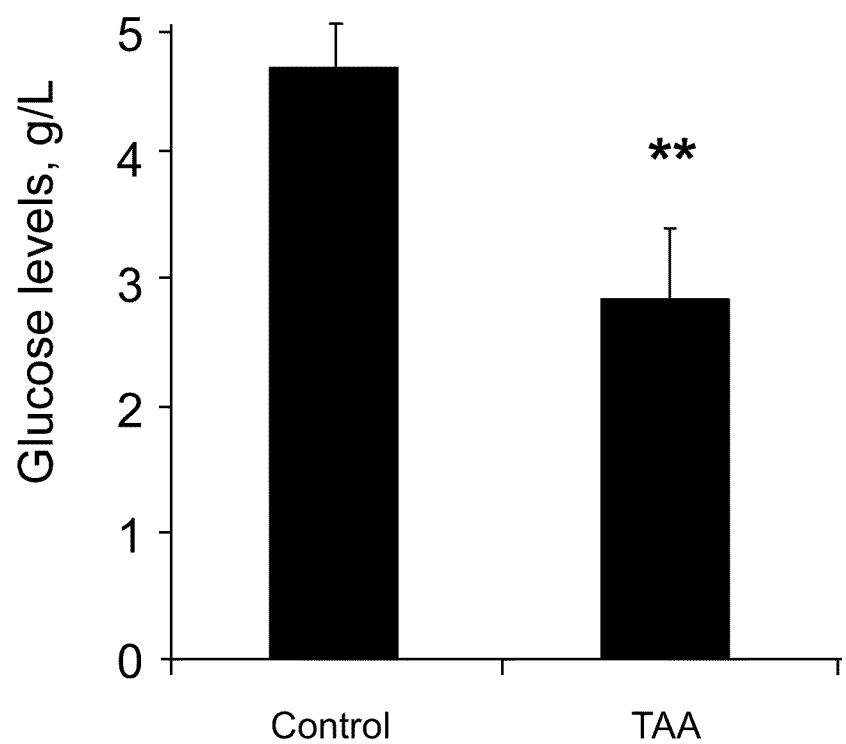
Figure 4A:
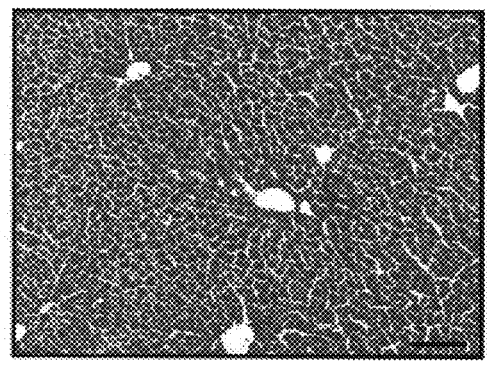
FIGS. 4A-F depict histopathological changes in the liver after treatment with TAA. 4A, normal mouse liver histology-score =0; 4B, mild centrilobular necrosis/apoptosis (score=1)
Figure 4B:
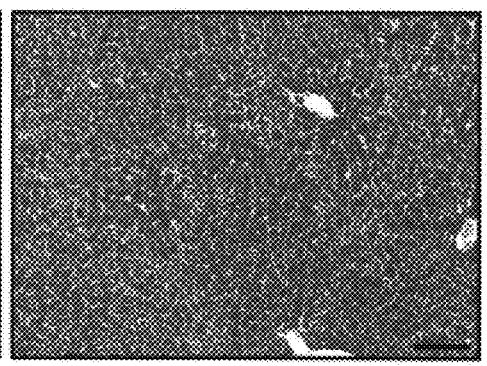
Figure 4C:
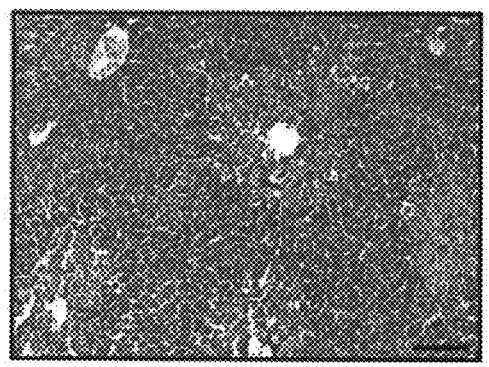
Figure 4D:
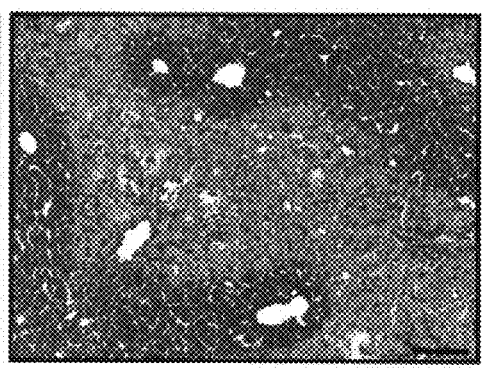
Figure 4E:
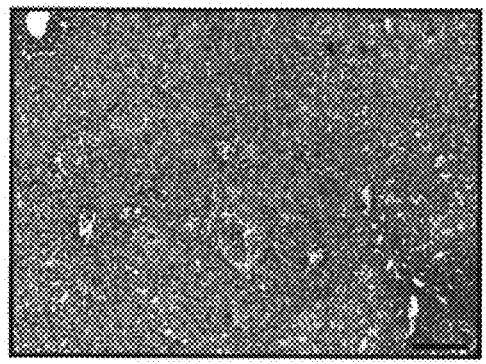
Figure 4F:
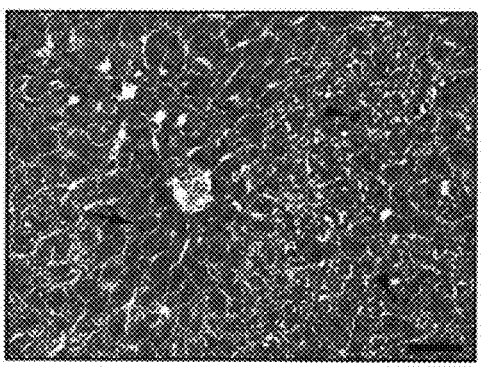

To investigate the possibility that the neural benefits of AICAR and THC might also result from peripheral effects (i.e. improvement of liver function) rather than cerebral function, we studied their effects on liver function. Animals treated with TAA exhibited hyperammonemia as a result of the liver dysfunction; AICAR and THC treatment had no effect on the ammonia level (FIG. 3A). Bilirubin levels and liver enzymes activity are the most commonly used laboratory markers of liver function. TAA treated mice demonstrated increased levels of bilirubin (FIG. 3B), alanine transaminase (ALT) (FIG. 3C), aspartate aminotransferase (AST) (FIG. 3D) and gamma-glutamyltransferase (GGT) (FIG. 3E). Neither AICAR nor THC ameliorated these markers indicating lack of direct action on liver recovery. Glucose analysis revealed a systemic hypoglycemia following TAA treatment (FIG. 3F) providing additional evidence for the metabolic energy impairment characterizing experimental hepatic encephalopathy.

Example 4

Capsaicin Improves Impaired Markers of Hepatic Function in Experimental Hepatic Encephalopathy The surprising fact that THC, which has about equal affinity for the CB1 and CB2 receptor, was effective in the treatment of induced hepatic encephalopathy in animal models, motivated us to investigate other compounds known to interact with receptors other than the endocannabinoid receptors. For example, capsaicin, suggested by Di Marzo et al (1998) to interact with the endocannabinoid system, acts on neural cells via vanilloid receptors subtype 1 (VR1, also known as transient receptor potential 1 TRPV1), a non-selective cation channel, which can be blocked by capsazepine. Thus, TAA treated mice were administered different agonist/antagonists and capsaicin and their effect on hepatic function was assessed.

First, histopathological changes were observed after the treatment with TAA. FIGS. 4A-F depict varying degrees of necrosis which were semi-quantitated as histopathological indices 1-4.

Second, the effect on hepatic function of different agents administered to the TAA treated animals was tested. Comparison of the histopathological indices assessed for each group indicated that amelioration of TAA-induced apoptosis/necrosis reached statistical significance (P<0.05) only with capsaicin treatment. However, inflammation was reduced also in HU308 and SR141716A—treated animals when compared to TAA-treated group, whereas, SR144528 treatment resulted in non-significant changes with regard to the inflammatory process.

The regenerative capacity of the liver in all cannabinoid receptor agonists or antagonists—treated groups was higher when compared to animals to which only TAA was administered, except capsaicin treated animals which exhibited significantly less hepatic regeneration (Table 1).

TABLE 1

Comparison of the frequency of cells showing apoptosis/necrosis, inflammation and regeneration in the liver.

| Groups comparison | Apoptosis | Inflammation | Regeneration |
|---|---|---|---|
| TAA vs normal | Increase ($p < 0.001$*) | Increase ($p < 0.001$*) | Increase ($p < 0.001$*) |
| TAA + capsaicin vs TAA | Decreased ($p < 0.005$*) | Decreased ($p < 0.01$*) | Decreased ($p < 0.001$*) |
| TAA + SR141716A vs TAA | NS** | Decreased ($p < 0.001$**) | Increased ($p < 0.005$*) |
| TAA + HU-308 vs TAA | NS* | Decreased ($p < 0.005$*) | Increased ($p < 0.001$*) |
| TAA + SR144528 vs TAA | NS* | NS* | Increased ($p < 0.05$*) |
| TAA + 2Ag vs TAA | NS* | Decreased ($p < 0.05$*) | Increased ($p < 0.05$*) |
| TAA + 2Ag + SR141716A vs TAA | NS* | Decreased ($p < 0.05$*) | Increased ($p < 0.05$*) |

*= Fisher's exact test;
**= Pearson's chi-square test

Example 5

CB1 Antagonist and CB2 Agonist Treatment Improve Markers of Hepatic Function

Figure 5A:
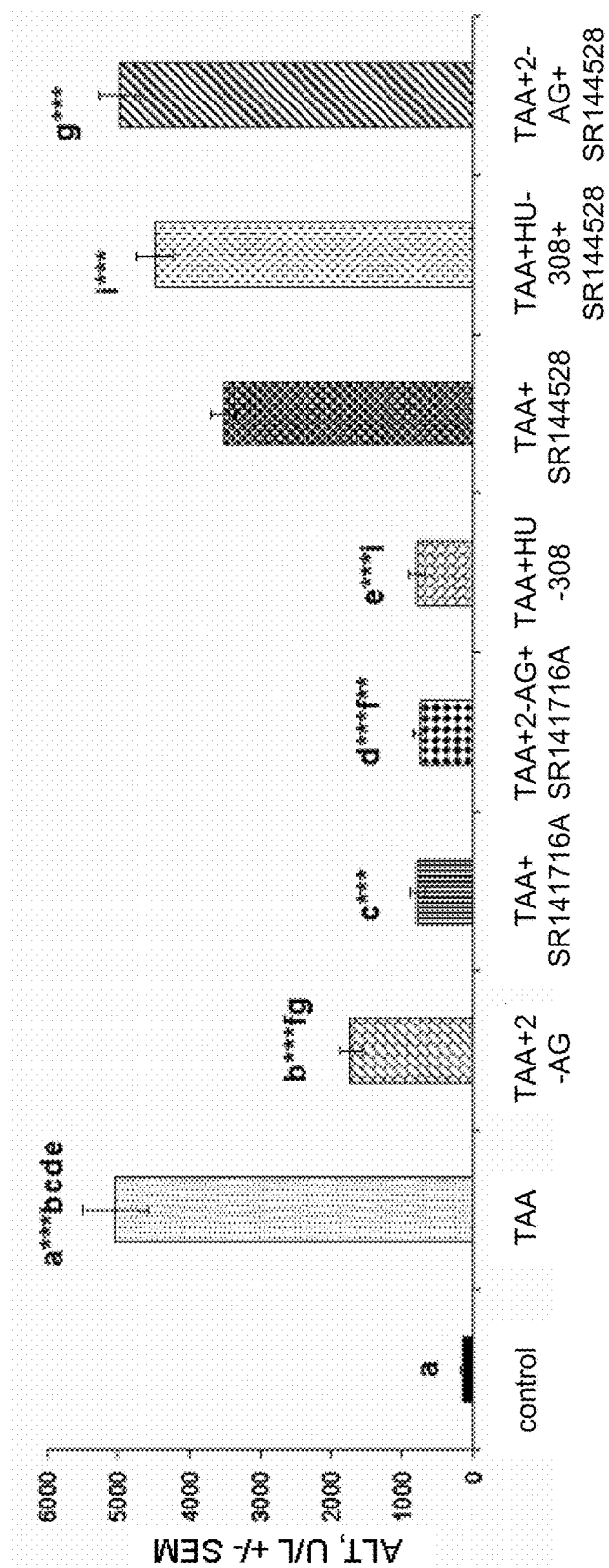
FIGS. 5A-B show TAA effect on (5A) alanine transaminase (ALT) and (5B) aspartate aminotransferase (AST) in mice treated with different cannabinoid receptor ligands.
Figure 5B:
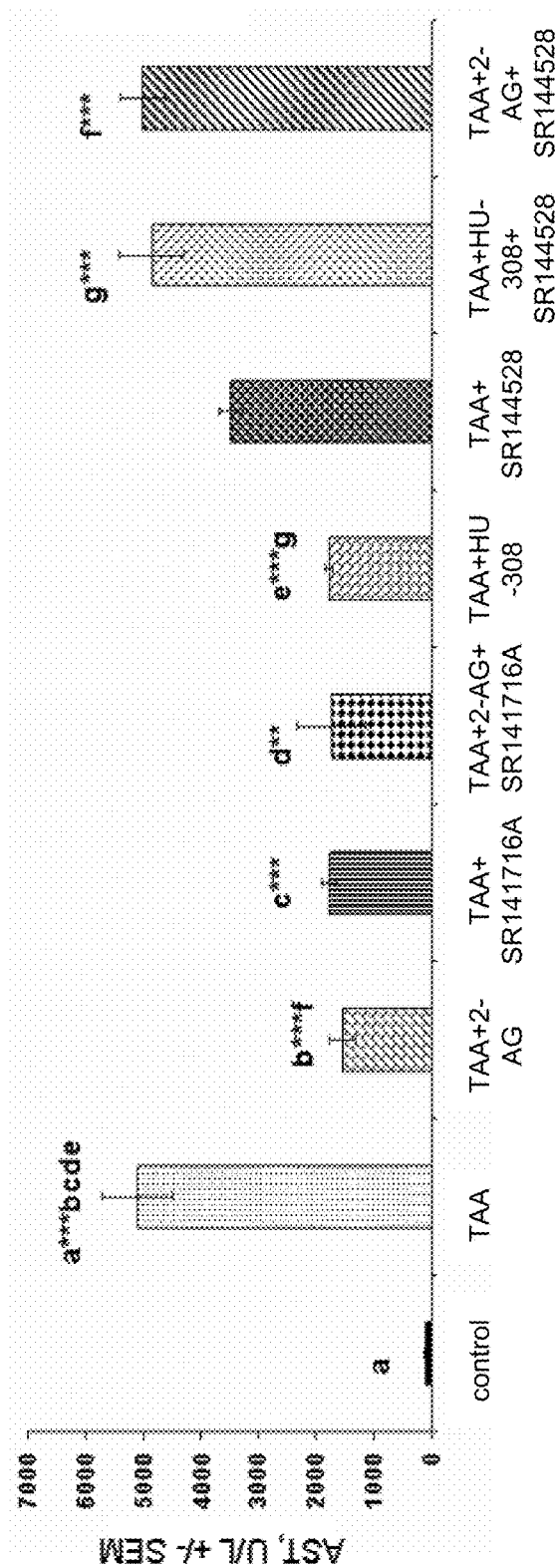

TAA treated mice demonstrated increased levels of alanine transaminase (ALT) (FIG. 5A) (see also FIG. 3C) and aspartate aminotransferase (AST) (FIG. 5B) (see also FIG. 3D); treatment of the TAA treated mice with 2-AG—a CB1 agonist, SR141716A—a CB1 antagonist, HU-308—a CB2 agonist, and SR144528—a CB2 antagonist, all significantly reduced ALT and AST levels. Moreover, 2-AG did not counteract the effect of SR141716A or SR144528, and HU-308 did not counteract the effect of SR144528. Thus, the results imply that the agonists/antagonists did not convey their effect specifically through the CB1 or CB2 receptors.

Example 6

Figure 6A:
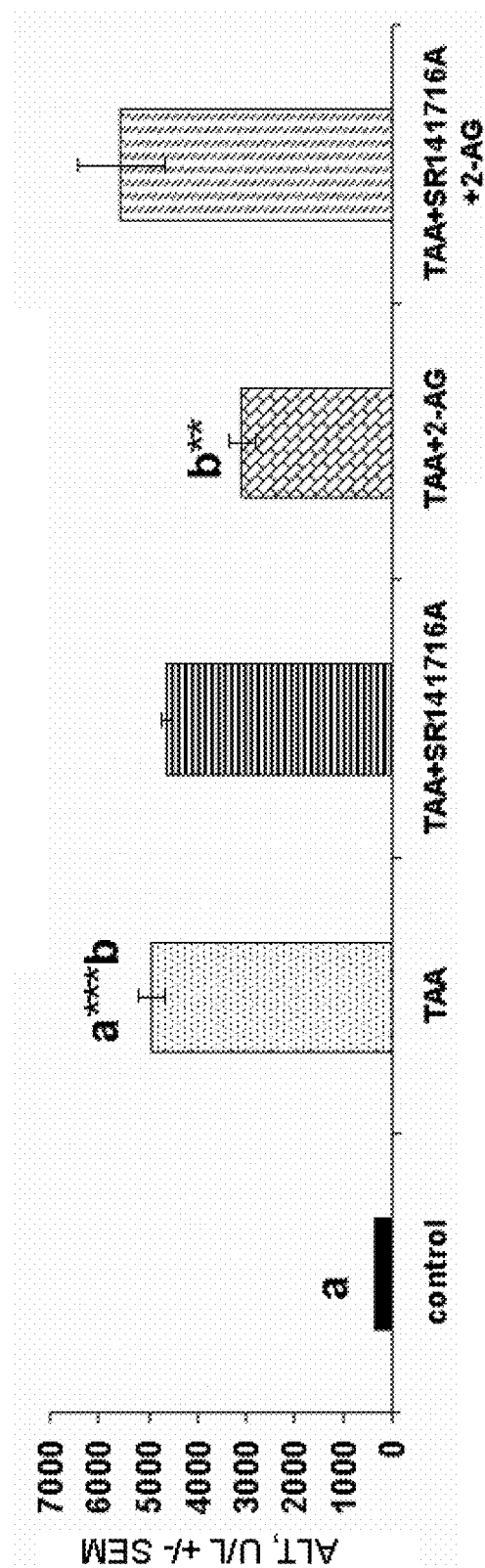
FIGS. 6A-B show effect of 2-arachidonoylglycerol (2-AG) and SR141716A on blood ALT (6A) and AST levels (6B) in TAA treated CB2-KO mice.

CB2 Agonist, but not CB1 Antagonist Treatment Improves Markers of Hepatic Function in CB2-KO Mice In the transgenic mice lacking the CB2 receptor, 2-AG but not SR141716A modestly but significantly reduced the ALT level and SR141716A blocked the effect of 2-AG (FIG. 6A), confirming that effect was achieved through the CB1 receptor.

Figure 6B:
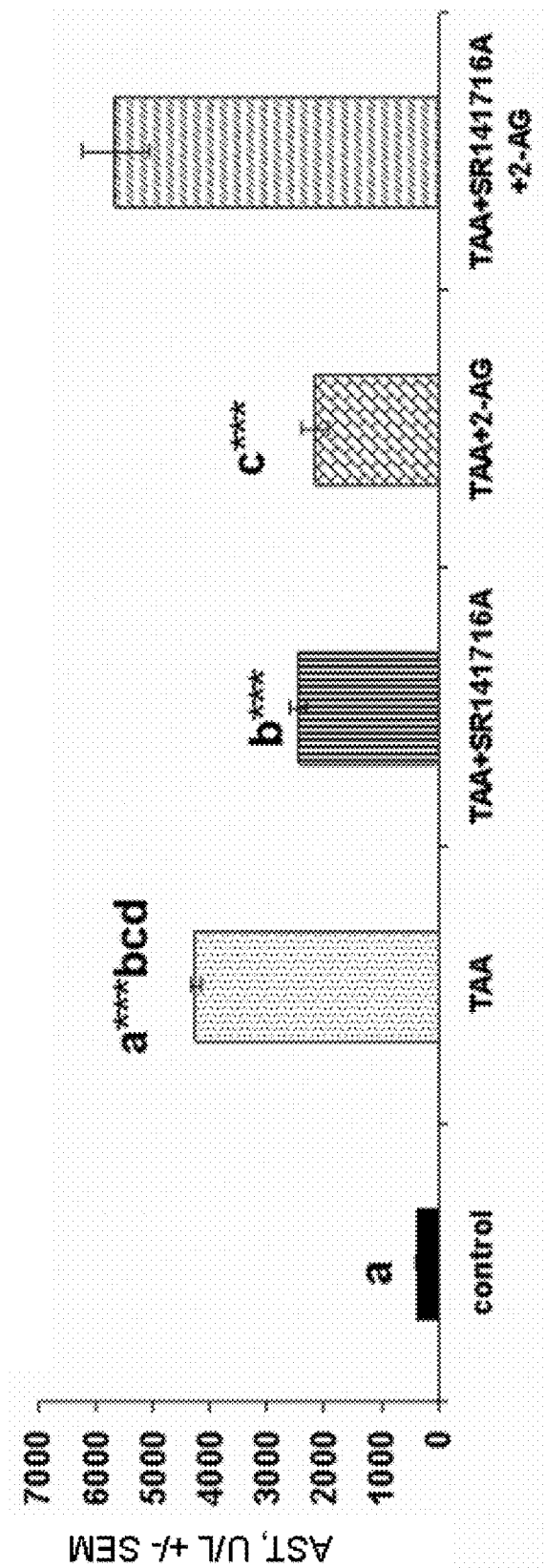

The effect of the endocannabioid agonist and antagonist on the second hepatic function marker tested, AST, was inconsistent with the result obtained for ALT in that both the CB1 antagonist SR141716A and the CB1 agonist 2-AG were effective in reducing its level (FIG. 6B). SR141716A abolished the effect of 2-AG, or vice-versa.

Example 7

Capsaicin Treatment Improves Markers of Hepatic Function

Figure 7A:
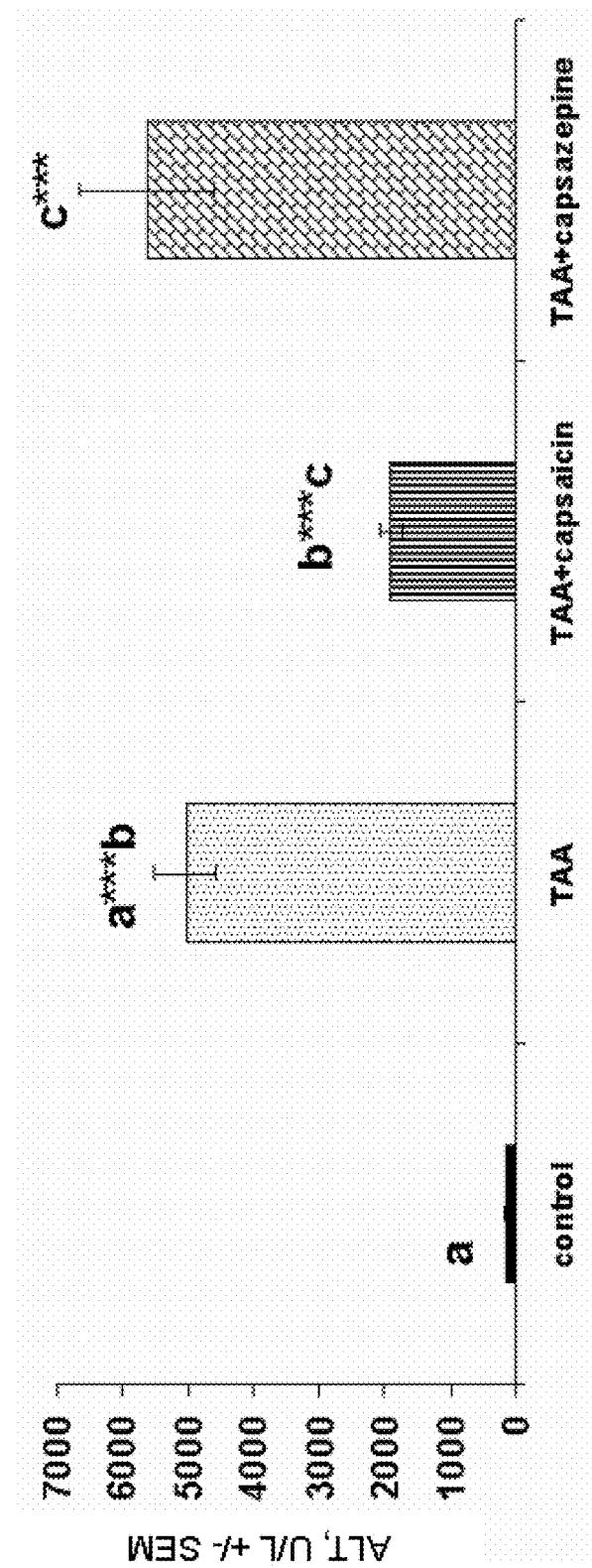
FIGS. 7A-B show that capsaicin significantly reduces both the ALT (7A) and the AST (7B) level in TAA treated mice.
Figure 7B:
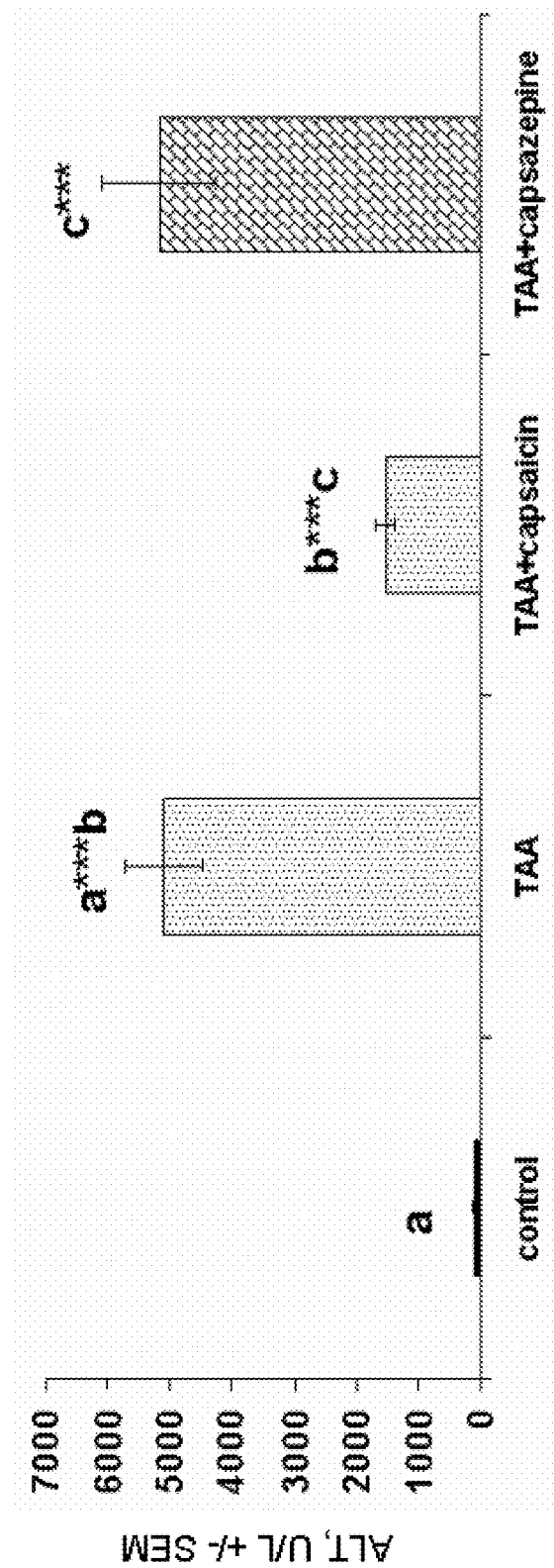

The results disclosed above imply that the effect observed with the endocannabioid agonist and antagonist may have been affected through another receptor than the CB1 receptor. We therefore tested the effect of capsaicin, which as mentioned above, has been suggested to interact with the endocannabinoid system. FIGS. 7A-B show that indeed, capsaicin significantly reduces both the ALT and the AST level in TAA treated mice. The effect of capsaicin is specifically affected through the VR1 receptor as evidenced by the abolishment of the effect of capsaicin by the VR1 antagonist capsazepine.

Example 8

Endocannabioid Agonist and Antagonist and Capsaicin Treatment Reduce Astrogliosis in TAA Treated Mice To assess whether endocannabioid agonist and antagonist and capsaicin treatment affect the important aspect of hepatic encephalopathy pathology—astrogliosis—TAA treated animals were treated with these compounds and hippocampus was stained for glial cells in naïve animals (FIG. 8A) and after treatment (FIGS. 8B-F).

Figure 8A:
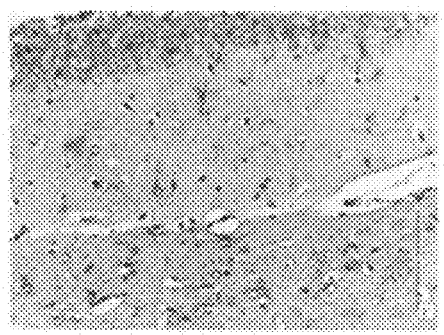
FIGS. 8A-F depict glial cell staining at the area of hippocampus in naïve animals (8A), and astrogliosis following TAA administration (8B-F). Hepatic encephalopathy induced intensive glial fibrillary acidic protein (GFAP, a marker for glial cells) staining intensity and increased process complexity. These changes were minimal following capsaicin—(8C), CB1 antagonist—(8D) and CB2 agonist—(8E) treatment, whereas CB2 antagonist administration (8F) did not alter either the number or morphology of activated astroglia compared to untreated animals (8B).
Figure 8B:
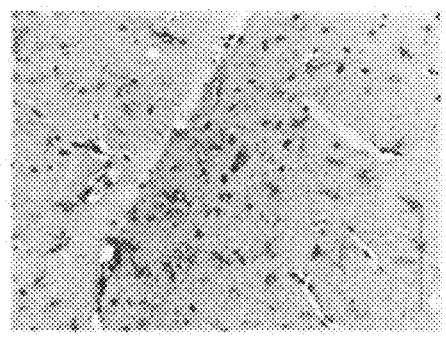
Figure 8C:
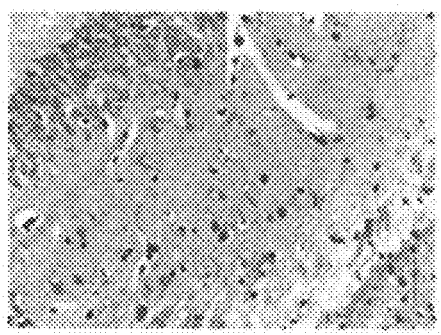
Figure 8D:
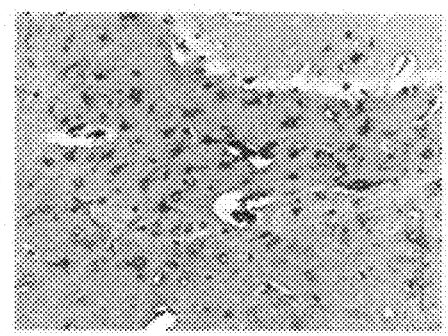
Figure 8E:
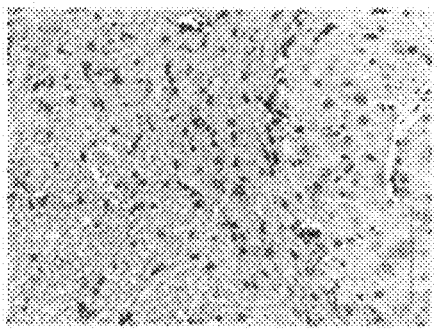
Figure 8F:
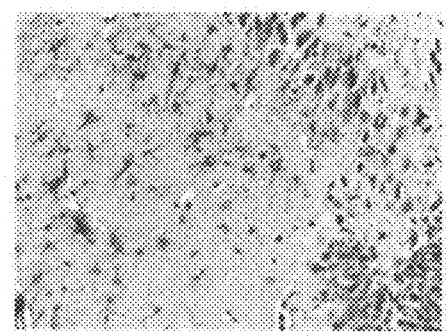

It was found that hepatic encephalopathy induced intensive glial fibrillary acidic protein (GFAP, a marker for glial cells) staining intensity and increased process complexity, i.e. more processes and increased branching (FIG. 8B) as compared with naïve animals (FIG. 8A). These changes were prevented following capsaicin—(FIG. 8C), CB1 antagonist (SR141716A)—(FIG. 8D) and CB2 agonist (HU-308)—(FIG. 8E) treatment, whereas CB2 antagonist (SR144528) administration (FIG. 8F) failed to prevent the hepatic encephalopathy induced changes and did not alter either the number or morphology of activated astroglia compared to untreated animals (FIG. 8B), as can be seen in Table 2, presenting the changes in quantitative terms.

TABLE 2

Quantification of the changes in astrogliosis following TAA and treatments with various compounds. (two-sided Fisher's exact test)

| Comparison | Direction of change |
|---|---|
| TAA vs normal | Increase ($p < 0.001$) |
| TAA + capsaicin vs TAA | Decrease ($p < 0.001$) |
| TAA + SR141716A vs TAA | Decrease ($p < 0.001$) |
| TAA + HU-308 vs TAA | Decrease ($p < 0.001$) |
| TAA + SR144528 vs TAA | NS |

Example 9

Figure 9A:
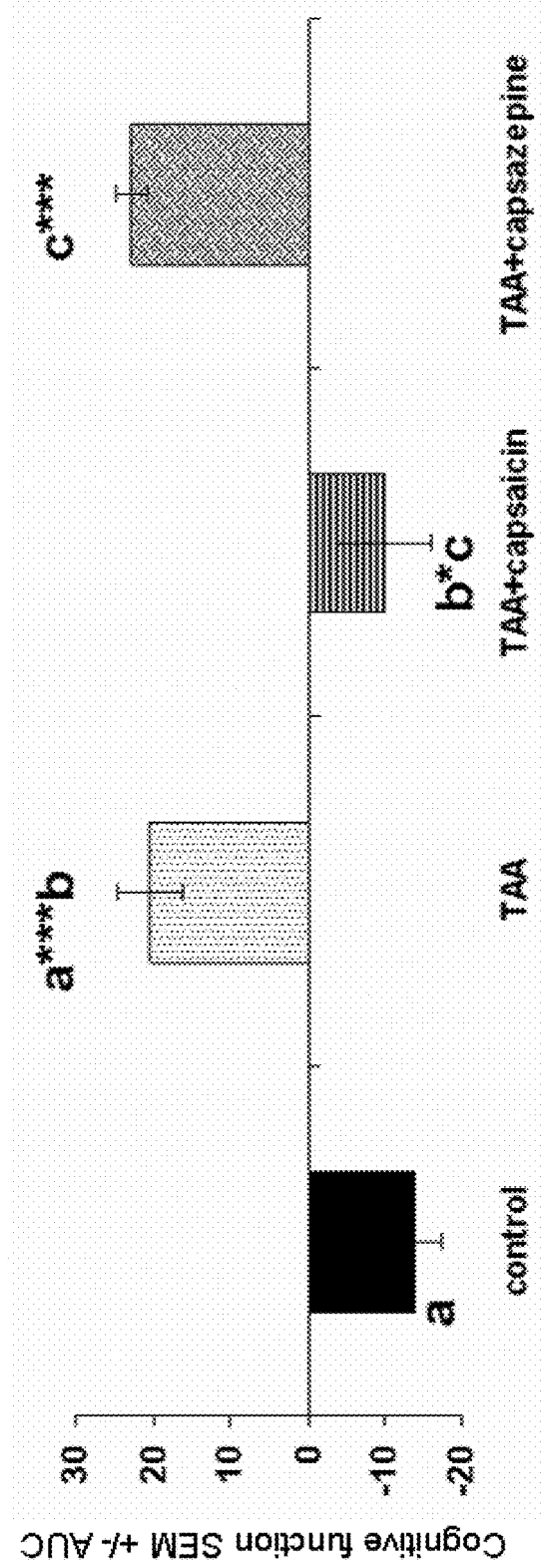
FIGS. 9A-C show that capsaicin significantly improves TAA-induced impaired cognitive function (9A), poor activity performances (9B) and reduced neurological score (9C).
Figure 9B:
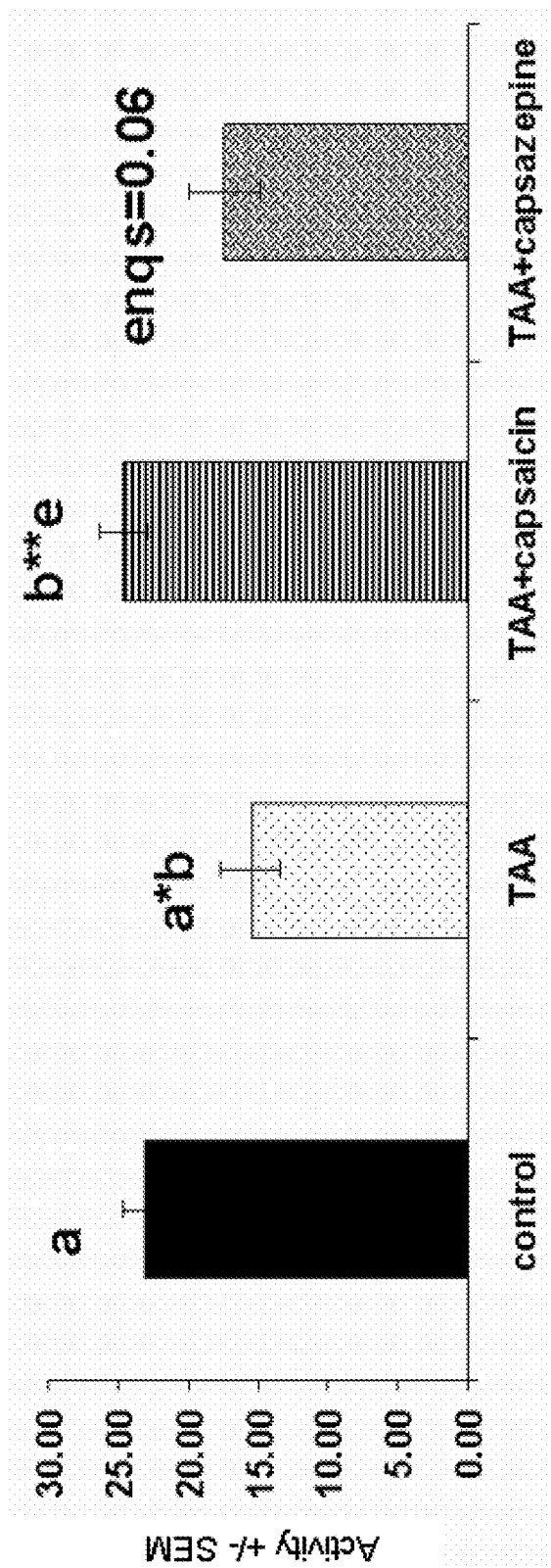
Figure 9C:
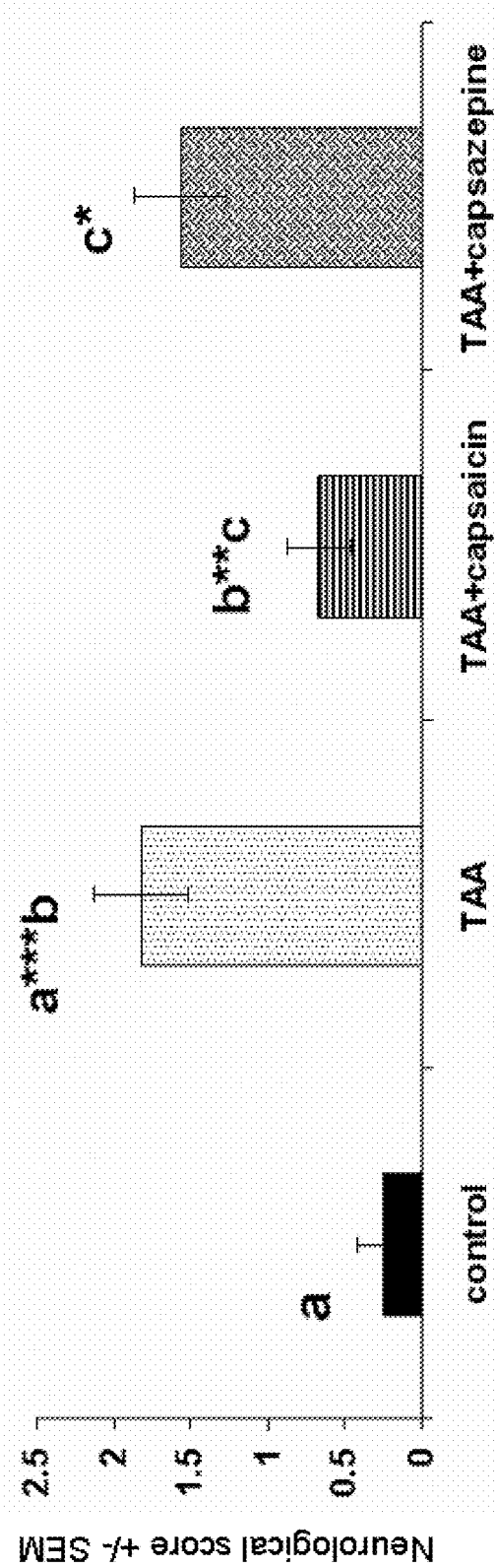

Capsaicin Improves Impaired Brain Function in Experimental Hepatic Encephalopathy Since treatment with capsaicin reduced astrogliosis in TAA treated mice, we were interested in assessing whether the treatment also had a positive effective on the impaired brain functions of hepatic encephalopathy mice. Following the treatment with capsaicin, TAA-induced impaired cognitive function was improved significantly (FIG. 9A), poor activity performances were restored (FIG. 9B) and the reduced neurological score was improved (FIG. 9C).

Example 10

Figure 10A:
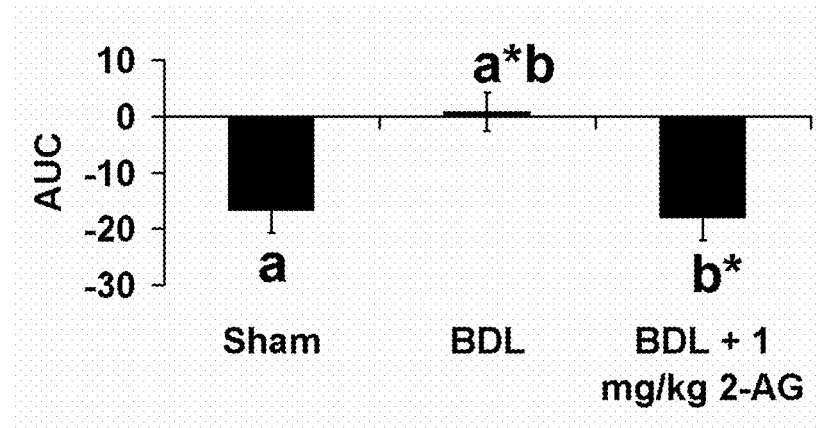
FIGS. 10A-B depict the effect of 2-AG treatment of chronic liver failure induced by bile duct ligation (BDL) on cognitive impairment (10A) and motor impairment (10B) relative to Sham operated animals. AUC, area under the curve.
Figure 10B:
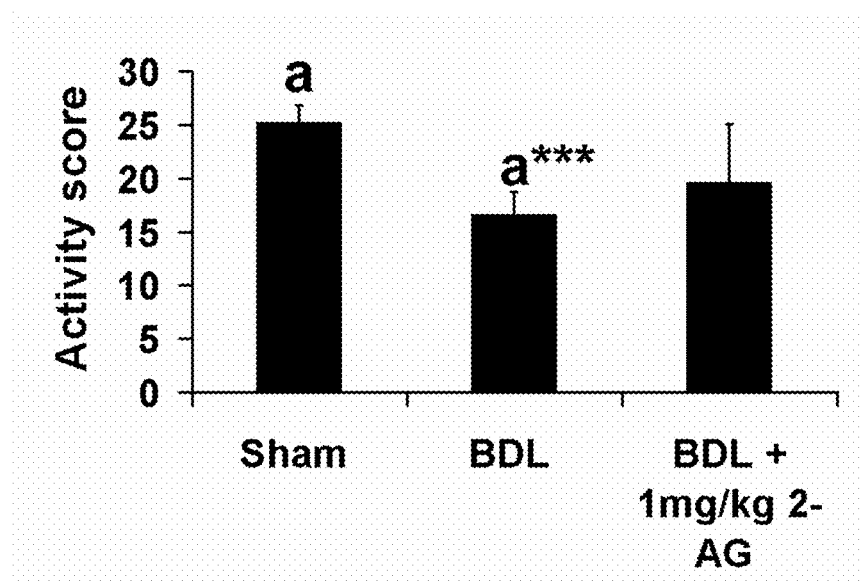

2-AG Treatment Effect on Cognitive Impairment Secondary to Biliary Cirrhosis and Motor Impairments As can be seen in FIGS. 10A-B, 2-AG effectively reversed cognitive impairments secondary to biliary cirrhosis in mice (FIG. 10A), but failed to reverse the motor impairments (FIG. 10B) which are also typical to this disorder.

Example 11

Cannabidiol Improves Impaired Brain and Liver Function in Experimental Hepatic Encephalopathy We decided to treat the animals with cannabidiol, an active ingredient of Cannabis Sativa devoid of adverse effects related to the CB1 receptor owing to its CB1-independent mechanism of action. Cannabidiol is also a very potent anti-inflammatory agent.

Chronic liver failure was induced by bile duct ligation (BDL) in female Sabra mice. Sham-operated mice served as controls. BDL animals were divided randomly to control and treatment groups, which received, respectively, saline and 5 mg/kg cannabidiol i.p. daily for 3 weeks.

Figure 11A:
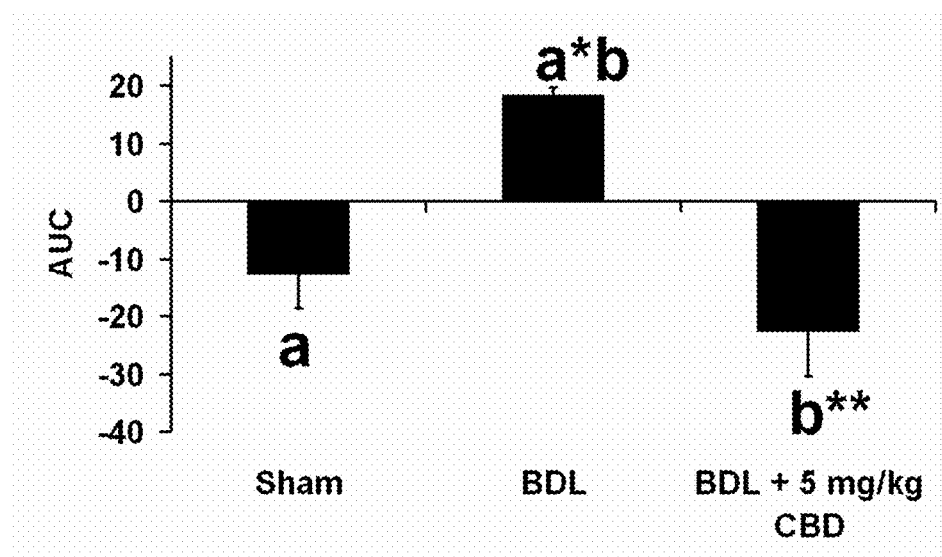
FIGS. 11A-B depict the effect of cannabidiol (CBD) treatment of chronic liver failure induced by bile duct ligation (BDL) on cognitive impairment (11A) and motor impairment (11) relative to Sham operated animals. AUC, area under the curve.
Figure 11B:
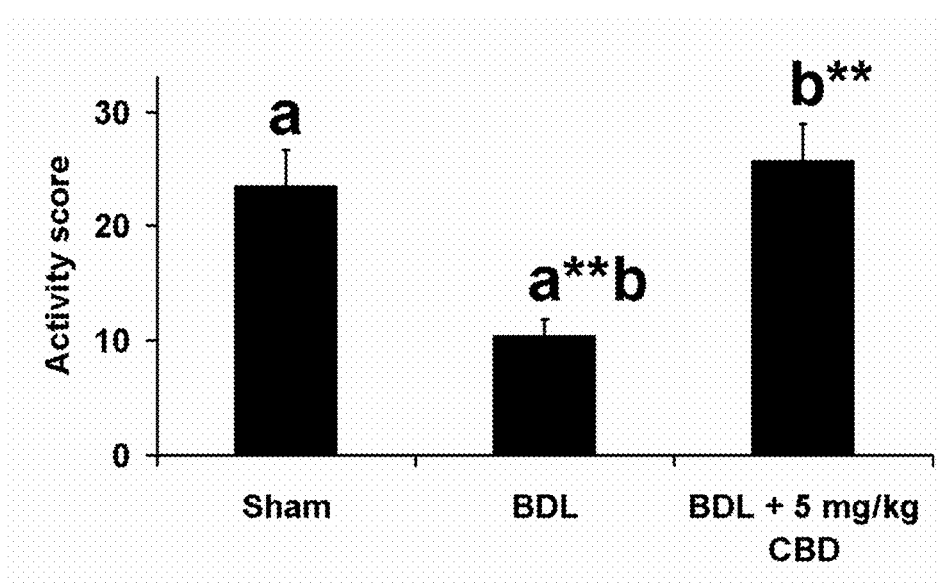
Figure 12A:
FIGS. 12A-B depict the effect of cannabidiol (CBD) treatment of chronic liver failure induced by bile duct ligation (BDL) on IL-1β mRNA level in the hippocampus relative to Sham operated animals. 12A, RT-PCR gel separation; 12B quantification of measurements done on the gel depicted in 12A. L19, ribosomal protein commonly used as invariant control gene; AUC, area under the curve.
Figure 12B:
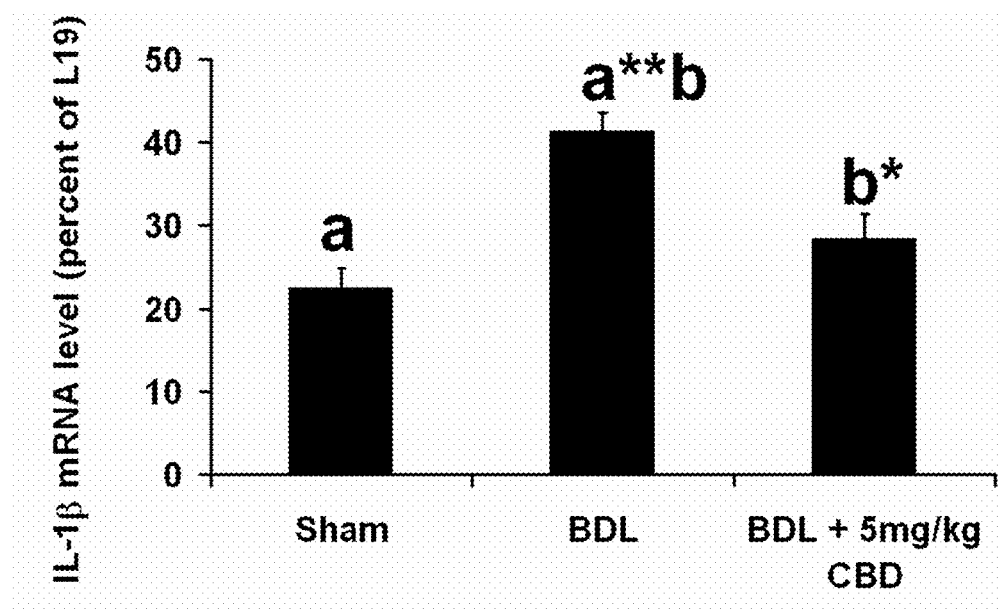

Two weeks post-surgery, the cognitive and the motor function of the mice were evaluated. Mice were decapitated 3 weeks post-surgery and their hippocampi were taken for analysis of IL-1b mRNA level by RT-PCR. The results clearly show that cognitive function (FIG. 11A) and motor activity (FIG. 11B) are impaired by BDL after 2 weeks and is restored by cannabidiol. Also, IL-1β mRNA level (normalized to ribosomal protein L19 mRNA levels; a commonly used invariant control gene) in the hippocampus is elevated following BDL and is restored by cannabidiol (FIGS. 12A-B).

Figure 13:
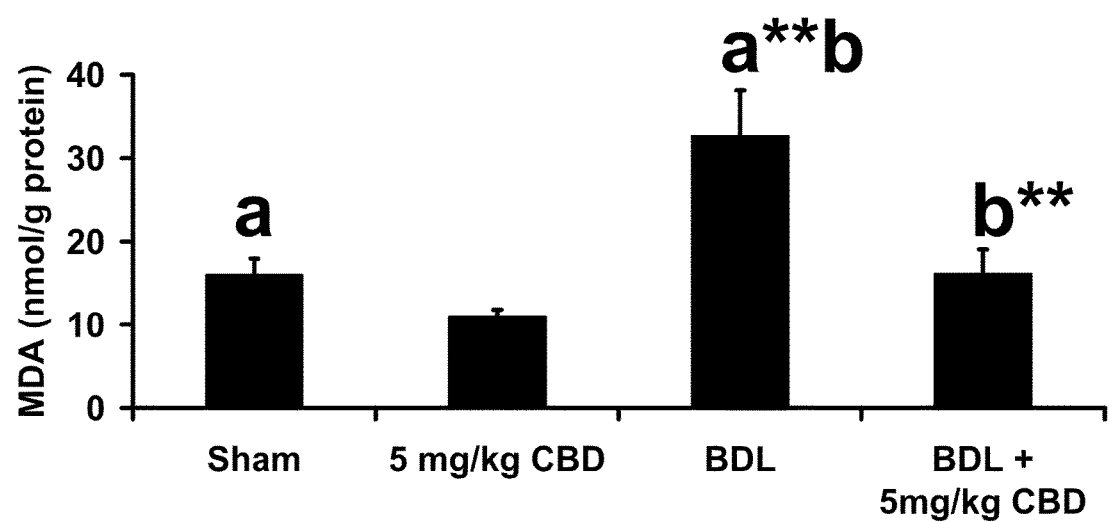
FIG. 13 shows the effect of cannabidiol (CBD) treatment of chronic liver failure induced by bile duct ligation (BDL) on oxidative stress in the liver. MDA, malondialdehyde.

Oxidative stress in liver tissue due to chronic liver failure induced by BDL was assessed by measuring malondialdehyde, a well accepted biomarker for oxidative stress. As can be seen in FIG. 13, oxidative stress is elevated following BDL and is restored by cannabidiol. As oxidative stress is commonly known to be involved in the development of cirrhosis (Ara et al., 2005) and treatment with cannabidiol reduces the oxidative stress, one can deduce that this treatment will prevent or slow down the development of cirrhosis.

In summary, after 2 weeks, bile duct ligation induced cognitive and motor deficits and increased oxidative stress in the liver, which were reversed by cannabidiol. In the hippocampus, which is responsible for learning and memory, there was an up-regulation of IL-1b mRNA following BDL, which was also reversed by cannabidiol, suggesting causal relationship between an inflammatory response in this region and impaired learning.

REFERENCES

Ara C, Kirimlioglu H, Karabulut A B, Coban S, Ay S, Harputluoglu M,

Kirimlioglu V, Yilmaz S. (2005) Protective effect of resveratrol against oxidative stress in cholestasis. J Surg Res.127(2):112-7

Avraham Y, Bonne O, Berry E M. Behavioral and neurochemical alterations caused by diet restriction—The effect of tyrosine administration in mice. Brain Research 1996; 732:133-144.

Avraham Y, Israeli E, Gabbay E, Okun A, Zolotarev O, Silberman I, Ganzburg V, Dagon Y, Magen I, Vorobia L, Pappo O, Mechoulam R, Ilan Y, Berry E M. Endocannabinoids affect neurological and cognitive function in thioacetamide-induced hepatic encephalopathy in mice. Neurobiol Dis. 2006 January; 21(1):237-45.

Baker D, Pryce G, Giovannoni G, Thompson A J. The therapeutic potential of cannabis. Review. Lancet Neurol 2003;2:291-298.

Barbiroli B, Gaiani S, Lodi R, Iotti S, Tonon C, Clementi V, Donati G, Bolondi L. Abnormal brain energy metabolism shown by in vivo phosphorus magnetic resonance spectroscopy in patients with chronic liver disease. Brain Res Bull 2002;59:75-82.

Bergold P J, Sweatt J D, Winicov I, Weiss K R, Kandel E R, Schwartz J H. Protein synthesis during acquisition of long-term facilitation is needed for the persistent loss of regulatory subunits of the Aplysia cAMP-dependent protein kinase. Proc Natl Acad Sci USA. 1990;87:3788-91.

Bernard A, Roger D, Luigi C, and Ramon L. Actinomycin D Blocks Formation of Memory of shock-avoidance in Goldfish. Science 1967;158: 3808,1600-1601

Berry E M, Mechoulam R. Tetrahydrocannabinol and endocannabinoids in feeding and appetite. Review. Pharmacol Ther 2002;95:185-190.

Bezuglov V, Bobrov M, Gretskaya N, Gonchar A, Zinchenko G, Melck D, Bisogno T, Di Marzo V, Kuklev D, Rossi J C, Vidal J P, Durand T. Synthesis and biological evaluation of novel amides of polyunsaturated fatty acids with dopamine Bioorg Med Chem Lett 2001;1.1:447-449

Bisogno T, Melck D, Bobrov M Yu, Gretskaya N M, Bezuglov V V, De Petrocellis L, Di Marzo V. N-Acyl-dopamines: novel synthetic CB(1) cannabinoid-receptor ligands and inhibitors of anandamide inactivation with cannabimimetic activity in vitro and in vivo. Biochem J 2000; 351:817-824.

Cheer J F, Wassum K M, Heien M L, Phillips, P E, Wightman, R M. Cannabinoids enhance subsecond dopamine release in the nucleus accumbens of awake rats. J Neurosci 2004;24:4393-4400.

Chen Y, Constantini S, Trembovler V, Weinstock M, Shohami E. An experimental model of closed head injury in mice: pathophysiology, histopathology and cognitive deficits. J Neurotrauma 1996;13:557-568.

Costa-Mattioli M, Gobert D, Harding H, Herdy B, Azzi M, Bruno M, Bidinosti M, Ben Mamou C, Marcinkiewicz E, Yoshida M, Imataka H, Cuello A C, Seidah N, Sossin W, Lacaille J C, Ron D, Nader K, Sonenberg N. Translational control of hippocampal synaptic plasticity and memory by the eIF2alpha kinase GCN2. Nature. 2005;436:1166-73.

Dagon Y, Avraham Y, Berry E M. AMPK activation regulates apoptosis, adipogenesis, and lipolysis by eIF2alpha in adipocytes. Biochem Biophys Res Commun. 2006;340:43-7.

Dagon Y, Avraham Y, Magen I, Gertler A, Ben-Hur T, Berry E M. Nutritional status, cognition, and survival: a new role for leptin and AMP kinase. J Biol Chem 2005;280: 42142-42148.

Devane W A, Hanus L, Breuer A, Pertwee R G, Stevenson L A, Griffin G, Gibson D, Mandelbaum A, Etinger A, Mechoulam R. Isolation and structure of a brain constituent that binds to the cannabinoid receptor. Science 1992;258: 1946-1949.

Folbergrova J, Zhao Q, Katsura K, Siesjo B K. N-tert-butyl-alpha-phenylnitrone improves recovery of brain energy state in rats following transient focal ischemia. Proc Natl Acad Sci USA. 1995;92:5057-5061.

Foretz M, Taleux N, Guigas B, Horman S, Beauloye C, Andreelli F, Bertrand L, Viollet B. (2006) Regulation of energy metabolism by AMPK: a novel therapeutic approach for the treatment of metabolic and cardiovascular diseases. Med Sci (Paris) 22(4):381-8.

Fride E, Mechoulam R. Pharmacological activity of the cannabinoid receptor agonist, anandamide, a brain constituent. Eur J Pharmacol 1993;231:313-314.

Gaoni Y and Mechoulam R Isolation, structure and partial synthesis of an active constituent of hashish. J Am Chem Soc 1964;86:1646-7

Gerber T, Schomerus H. Hepatic encephalopathy in liver cirrhosis: pathogenesis, diagnosis and management. Review. Drugs 2000;60:1353-1370.

Gerdeman G L, Partridge J G, Lupica C R, Lovinger D M. It could be habit forming: drugs of abuse and striatal synaptic plasticity. Review. Trends Neurosci 2003;26: 184-192.

Hanus, A. Breuer, S. Tchilibon, S. Shiloah, D. Goldenberg, M. Horowitz, R. G. Pertwee, R. A. Ross, R. Mechoulam, and E. Fride (1999) PNAS 96:14228-14233.

Hardie D G, Carling D. The AMP-activated protein kinase—fuel gauge of the mammalian cell? Review. Eur J Biochem 1997;246:259-273.

Hardie D G. The AMP-activated protein kinase pathway—new players upstream and downstream. Review. J Cell Sci 2004;117:5479-5487.

Hawley S A, Davison M, Woods A, Davies S P, Beni R K, Carling D, and Hardie D G. Characterization of the AMP-activated protein kinase kinase from rat liver and identification of threonine 172 as the major site at which it phosphorylates AMP-activated protein kinase. J Biol Chem 271: 27887-27879, 1996

Hoyer S. Abnormalities in brain glucose utilization and its impact on cellular and molecular mechanisms in sporadic dementia of Alzheimer type Ann N Y Acad Sci 1993;695: 77-80.

Iversen L L. The Science of Marijuana (Oxford Univ. Press, New York, 2000), p. 36.

Julien B, Grenard P, Teixeira-Clerc F, Van Nhieu J T, Li L, Karsak M, Zimmer A, Mallat A, Lotersztajn S. Antifibrogenic role of the cannabinoid receptor CB2 in the liver. Gastroenterology. 2005;3:128:742-55.

Kola B, Hubina E, Tucci S A, Kirkham T C, Garcia E A, Mitchell S E, Williams L M, Hawley S A, Hardie D G, Grossman A B, Korbonits M. Cannabinoids and ghrelin have both central and peripheral metabolic and cardiac effects via AMP-activated protein kinase. J Biol Chem. 2005;280: 25196-201.

Martin B R. Role of lipids and lipid signaling in the development of cannabinoid tolerance. Review. Life Sci 2005;77:1543-1558.

Matsuda L A, Lolait S J, Brownstein M J, Young A C, Bonner T I. Structure of a cannabinoid receptor and functional expression of the cloned cDNA. Nature 1990;346: 561-564.

Minokoshi Y, Alquier T, Furukawa N, Kim Y B, Lee A, Xue B, Mu J, Foufelle F, Ferre P, Birnabaum M J, Stuck B J, Kahn B B. AMP-kinase regulates food intake by responding to hormonal and nutrient signals in the hypothalamus. Nature 2004;428:569-574.

Mishima K, Egashira N, Hirosawa N, Fujii M, Matsumoto Y, Iwasaki K, Fujiwara M. Characteristics of learning and memory impairment induced by delta9-tetrahydrocannabinol in rats. Jpn J Pharmacol. 2001;87:297-308.

Mizuno Y, Ikebe S, Hattori N, Nakagawa-Hattori Y, Mochizuki H, Tanaka M. Role of mitochondria in the etiology and pathogenesis of Parkinson's disease. Review. Biochim Biophys Acta 1995;1271:265-274.

Molina-Holgado F, Pinteaux E, Heenan L, Moore J D, Rothwell N J, Gibson R M. Neuroprotective effects of the synthetic cannabinoid HU-210 in primary cortical neurons are mediated by phosphatidylinositol 3-kinase/AKT signaling. Mol Cell Neurosci. 2005;28:189-94.

Olton D S, Samuelson R J. Remembrance of places passed: Spatial memory in rats. J Exp Psychol Anim Behav Process 1976;2:97-116.

Ott P, Clemmesen O, Larsen F S. Cerebral metabolic disturbances in the brain during acute liver failure: from hyperammonemia to energy failure and proteolysis. Review. Neurochem Int 2005;47:13-18.

Pagotto U, Vicennati V, Pasquali R. The endocannabinoid system and the treatment of obesity. Ann Med. 2005;37: 270-5. Review.

Pick C G, Yanai J. Eight arm maze for mice. Int J Neurosci 1983;21:63-66.

Ross B D, et al. 31P spectroscopic imaging shows energy deficit of thalamus in chronic hepatic encephalopathy. In: Book of Abstracts, Annual Meeting of the Society of Magnetic Resonance in Medicine, Amsterdam; 1989: 465.

Sulcova E, Mechoulam R, Fride E. Biphasic effects of anandamide. Pharmacol Biochem Behav 1998;59:347-353.

Teixeira-Clerc F, Julien B, Grenard P, Tran Van Nhieu J, Deveaux V, Li L, Serriere-Lanneau V, Ledent C, Mallat A, Lotersztajn S. CB1 cannabinoid receptor antagonism: a new strategy for the treatment of liver fibrosis. Nat Med. 2006; 6:12:671-6.

Xiong Y, Peterson P L, Lee C P. Alterations in cerebral energy metabolism induced by traumatic brain injury. Review. Neurol Res 2001;23:129-138.

Zimmermann C, Ferenci P, Pifl C, Yurdaydin C, Ebner J, Lassmann H, Roth E, Hortangl H. Hepatic encephalopathy in thioacetamide-induced acute liver failure in rats: characterization of an improved model and study of amino acidergic neurotransmission. Hepatology 1989;9:594-601.

The invention claimed is:

1. A method for reducing oxidative stress in liver tissue of a subject with non-alcoholic steatohepatitis but without fibrosis or cirrhosis, comprising administering a therapeutically effective amount of cannabidiol to the subject.

2. The method according to claim 1, wherein said cannabidiol is administered orally, parenterally, sublingually, or by inhalation.

3. A method in accordance with claim 1, wherein said non-alcoholic steatohepatitis is caused by fatty liver.

4. A method of treatment of non-alcoholic steatohepatitis, comprising administering to a subject in need an effective amount of cannabidiol, wherein the subject does not have fibrosis or cirrhosis.

* * * * *